(12) United States Patent
Kovriguine

(10) Patent No.: US 10,139,344 B2
(45) Date of Patent: Nov. 27, 2018

(54) ADAPTER FOR A CELL HOLDER OF A SPECTROFLUOROMETER

(71) Applicant: Marquette University, Milwaukee, WI (US)

(72) Inventor: Evgueni Kovriguine, Brookfield, WI (US)

(73) Assignee: Marquette University, Milwaukee, WI (US)

( * ) Notice: Subject to any disclaimer, the term of this patent is extended or adjusted under 35 U.S.C. 154(b) by 9 days.

(21) Appl. No.: 15/595,342

(22) Filed: May 15, 2017

(65) Prior Publication Data

US 2017/0315057 A1 Nov. 2, 2017

Related U.S. Application Data

(63) Continuation-in-part of application No. PCT/US2015/060658, filed on Nov. 13, 2015.

(60) Provisional application No. 62/186,449, filed on Jun. 30, 2015, provisional application No. 62/079,273, filed on Nov. 13, 2014.

(51) Int. Cl.
*G01N 21/64* (2006.01)
*G01N 33/487* (2006.01)

(52) U.S. Cl.
CPC ....... *G01N 21/645* (2013.01); *G01N 21/6428* (2013.01); *G01N 33/487* (2013.01); *G01N 2021/6439* (2013.01); *G01N 2021/6482* (2013.01)

(58) Field of Classification Search
CPC ............ G01N 21/645; G01N 21/6428; G01N 33/487; G01N 2021/6439; G01N 2021/6482
See application file for complete search history.

(56) References Cited

U.S. PATENT DOCUMENTS

| 4,153,369 A | * | 5/1979 | Kallet | G01N 21/31 250/461.1 |
| 8,049,884 B2 | * | 11/2011 | Tsukuda | G01N 21/251 356/244 |
| 9,279,746 B2 | * | 3/2016 | Wynn | G01N 21/05 |

(Continued)

FOREIGN PATENT DOCUMENTS

| CN | 102072880 A | 5/2011 |
| JP | 05126722 A | 5/1993 |

(Continued)

OTHER PUBLICATIONS

Bagatolli LA (2007) Membranes and Fluorescence Microscopy. In: C.D. Geddes (ed.), editor. Reviews in Fluorescence. pp. 33-51.

(Continued)

*Primary Examiner* — Marcus Taningco
*Assistant Examiner* — Djura Malevic
(74) *Attorney, Agent, or Firm* — Andrus Intellectual Property Law, LLP

(57) ABSTRACT

Disclosed herein are spectrofluorometric adaptors for cell holders in spectrofluorometers and uses of the adapters in spectrofluorometric methods that enable fluorescence detection from surfaces of a microcell in conventional horizontal-beam spectrofluorometers equipped with standard cell holders and having multiple excitation channels.

20 Claims, 10 Drawing Sheets

(56) References Cited

U.S. PATENT DOCUMENTS

2010/0221838 A1  9/2010  Burgess et al.

FOREIGN PATENT DOCUMENTS

RU  79181 U1  12/2008
WO  2009/055940 A1  5/2009

OTHER PUBLICATIONS

Brian AA, McConnell HM (1984) Allogeneic stimulation of cytotoxic T cells by supported planar membranes. Proc Natl Acad Sci U S A 81: 6159-6163.
Cremer PS, Boxer SG (1999) Formation and Spreading of Lipid Bilayers on Planar Glass Supports. The Journal of Physical Chemistry B 103: 2554-2559.
Galush WJ, Nye JA, Groves JT (2008) Quantitative fluorescence microscopy using supported lipid bilayer standards. Biophys J 95: 2512-2519.
Hell SW, Wichmann J (1994) Breaking the diffraction resolution limit by stimulated emission: stimulated-emission-depletion fluorescence microscopy. Optics Letters 19: 780-782.
Herschel FW (1845) On a case of superficial colour presented by a homogeneous liquid internally colorless. Philosophical Transactions of the Royal Society of London 135: 143-145.
Iversen L, Tu H-L, Lin W-C, Christensen SM, Abel SM, et al. (2014) Ras activation by SOS: Allosteric regulation by altered fluctuation dynamics. Science 345: 50-54.
Kastantin M, Walder R, Schwartz DK (2012) Identifying Mechanisms of Interfacial Dynamics Using Single-Molecule Tracking. Langmuir 28: 12443-12456.
Kinnunen P, Alakoskela J-M, Laggner P, Nejat D (2003) Phase Behavior of Liposomes. Methods in Enzymology: Academic Press. pp. 129-147.
Lakowicz JR (2010) Principles of Fluorescence Spectroscopy: Springer. p. 954.
Lin W-C, Iversen L, Tu H-L, Rhodes C, Christensen SM, et al. (2014) H-Ras forms dimers on membrane surfaces via a protein-protein interface. Proceedings of the National Academy of Sciences 111: 2996-3001.
Pinto SN, Fernandes F, Fedorov A, Futerman AH, Silva LC, et al. (2013) A combined fluorescence spectroscopy, confocal and 2-photon microscopy approach to re-evaluate the properties of sphingolipid domains. Biochimica Et Biophysica Acta-Biomembranes 1828: 2099-2110.
Raicu V, Singh DR (2013) FRET Spectrometry: A New Tool for the Determination of Protein Quaternary Structure in Living Cells. Biophysical Journal 105: 1937-1945.
Tamm LK, McConnell HM (1985) Supported phospholipid bilayers. Biophysical Journal 47: 105-113.
Woodle MC, Papahadjopoulos D (1989) Liposome preparation and size characterization. Methods Enzymol 171: 193-217.
International Search Report and Written Opinion for PCT/US2015/060658 dated Mar. 31, 2016.
International Preliminary Report on Patentability for PCT/US2015/060658 dated May 26, 2017.

\* cited by examiner

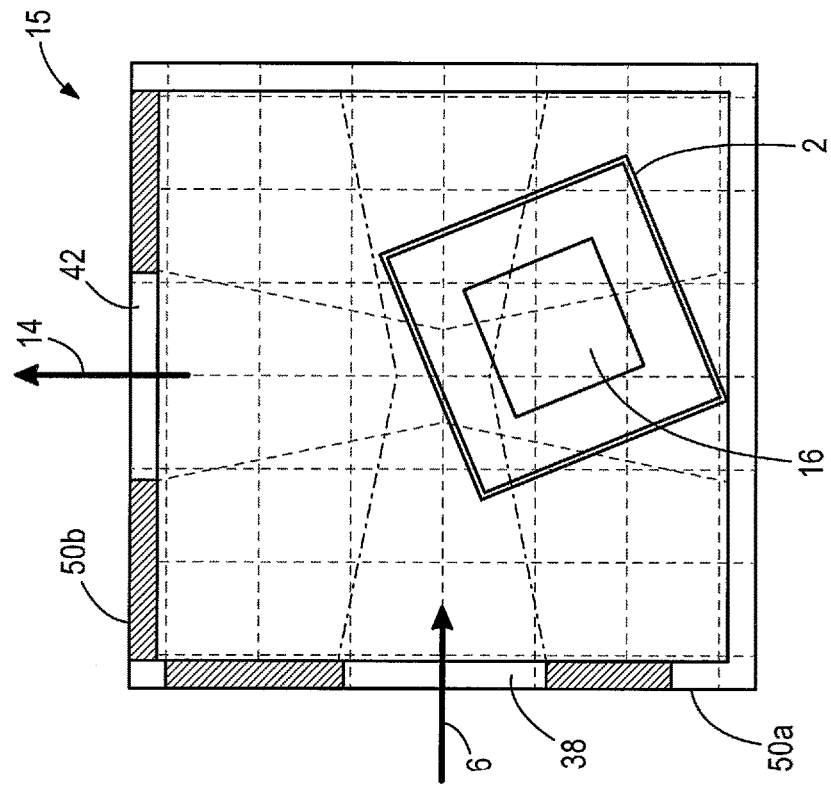
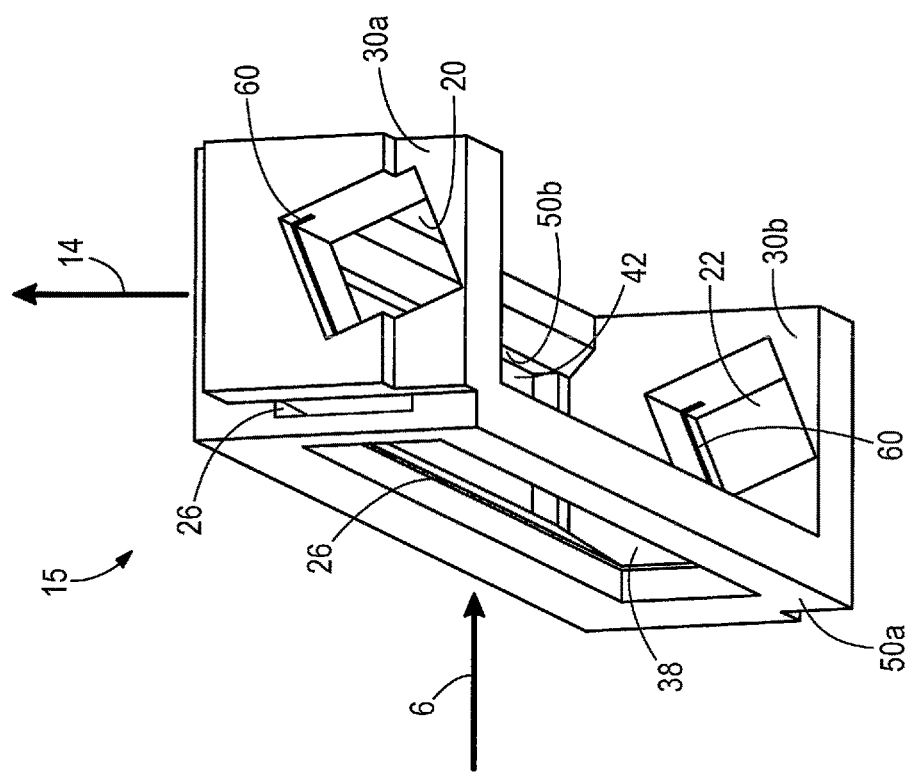
FIG. 4B
FIG. 4A

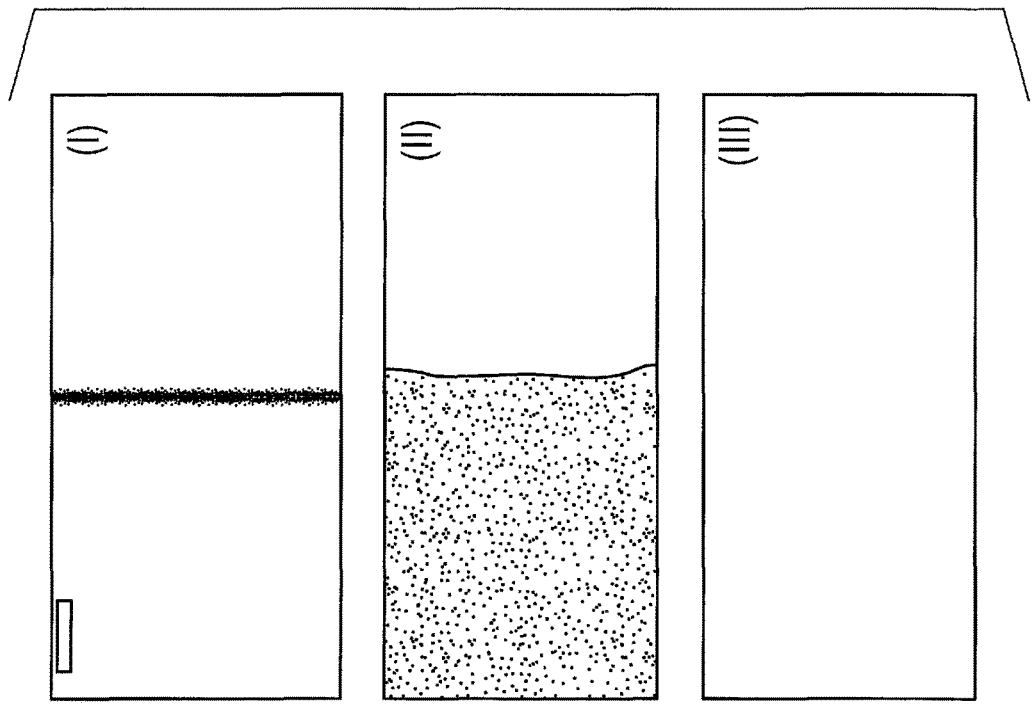
FIG. 8C
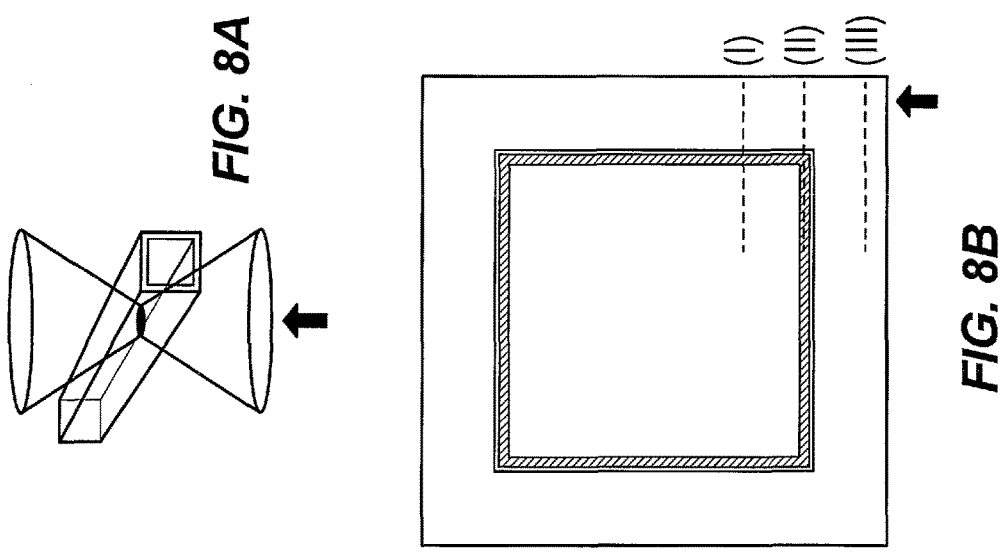
FIG. 8A
FIG. 8B

FIG. 9A  FIG. 9B

ADAPTER FOR A CELL HOLDER OF A SPECTROFLUOROMETER

CROSS-REFERENCE TO RELATED PATENT APPLICATIONS

The present application is a continuation-in-part under 35 U.S.C. § 365(c) of International Application PCT/US2015/060658, filed on Nov. 13, 2015, and published as WO2016/077741 on May 19, 2016, which International Application claims the benefit of prior under 35 U.S.C. § 119(e) to U.S. Provisional Application No. 62/186,449, filed on Jun. 30, 2015, and U.S. Provisional Patent Application No. 62/079,273, filed on Nov. 13, 2014, the contents of which are incorporated herein by reference in their entireties.

BACKGROUND

The field of the invention relates to spectrofluorometry. In particular, the field of the invention relates to adapters for cell holders of spectrofluorometers, wherein the adapter is configured to hold and position a microcell in the cell holder.

Fluorescence spectroscopy is one of the most sensitive methods for detecting biologically important molecules such as proteins, metabolites, and signaling molecules. In fluorescence spectroscopy, a light photon hits a molecule in an excitation process where the energy of the photon may be absorbed and re-emitted by the molecule through fluorescence. Often, the wavelength of the emitted photon is significantly longer than the wavelength of the excitation photon, which manifests itself as fluorescence in a different color. For example, excitation with blue light may cause green fluorescence. This phenomenon allows for sensitive detection of molecules capable of fluorescence emission (i.e., "fluorophores") because the emitted light may be readily differentiated from the background, scattered excitation light on the basis of the wavelength of the fluorescence emission. Fluorescence measurements are used extensively in many laboratory and clinical assays. The instruments for fluorescence detection range from small benchtop devices specialized for specific analysis to large versatile setups that enable detection of multiple fluorophores in samples and analysis of the multiple fluorophores' properties.

Fluorescence measurement typically is performed in solution. In a typical fluorometric measurement, a liquid sample is placed in a quartz or glass cell, and the cell then is placed in a cell holder of a fluorometer. The light beam from an excitation source then is directed into the quartz or glass cell through a side wall to illuminate the liquid sample inside the cell, which fluoresces. Fluorescence is emitted approximately equally in all directions and, generally, is much weaker than the excitation light, which may reflect and scatter upon illuminating the liquid sample. Therefore, in order to acquire accurate fluorescence measurements, it is important to separate the fluorescence signal from the reflected and scattered light of the excitation source.

To achieve the best separation, the most common design of the high-sensitivity spectrofluorometer involves detection of fluorescence at a 90° angle relative to the direction of the excitation light beam. (See FIG. 1A and FIG. 1B). As illustrated in FIG. 1A, an excitation beam 6 enters through an excitation aperture 8 in an excitation screen 9a and contacts the illuminated area 4 of a cell 2. Fluorophores in a sample solution 16 contained in the cell 2 are excited and emit fluorescence 14 which is detected through the observed area 10 of the cell 2 as the fluorescence passes through the emission aperture 12 in an emission screen 9b to a detector. As illustrated in FIG. 1A and FIG. 1B, to reduce contribution from scattered light, the excitation light or beam 6 typically is "trimmed" using an excitation screen 9a having a narrow, rectangular or linear, excitation aperture 8 which permits the excitation beam 6 to illuminate only a middle area of the cell 4 and to prevent the excitation beam 6 from illuminating the corners of the cell 2. The same technique is used for detecting fluorescence where an emission screen 9b having a narrow, rectangular or linear, excitation aperture 12 permits the emission beam 14 to exit the middle of the cell 2 as an observed area 10 and enter the emission channel of a detector for detection. As a result, the fluorescence signal is detected exclusively from the middle of the sample cell, which is referred to as the "working volume" (see FIG. 1B), thus avoiding detecting any light (fluorescence or scattered) originating from the cell walls. As indicated in FIG. 1B, a "working volume" 18 of the sample solution 16 is contacted by the excitation light 6 as it enters through an excitation aperture in the cell holder 11. Fluorescence emission 14 from the working volume can pass only through the emission aperture in the cell holder 11. This approach to measuring fluorescence from soluble molecules is utilized in the majority of highly sensitive commercial spectrofluorometers.

Difficulties in detecting fluorescence may arise due to high optical density and sample turbidity. For example, difficulties regarding high optical density may result when the concentration of the fluorophore in the solution is high enough that the solution absorbs all of the excitation light before it has a chance to reach the "working volume" in the middle of the cell, a phenomenon termed "inner filtering effect." The same difficulty may arise when turbidity in the sample due to suspended particles blocks the excitation beam. To enable observation of fluorescence in these situations, a conventional workaround involves illuminating the front surface of the cell and exposing the same surface to the emission channel. This workaround permits collection of the fluorescence signal from the portion of solution near the inner cell wall provided that the emission signal can be distinguished from the reflected and scattered excitation beam.

In recent years, some research has focused on the observation of fluorescence from solution-glass interfaces in order to investigate molecular structures absorbed on the glass surface (e.g., phospholipid bilayers). Most of these studies have been performed using horizontal glass slides where the solution drops are placed on top of the slide and observation are made from the bottom of the slide using fluorescence microscopes. The advantage of this setup is in its microscopic resolution of the surface details. However, the drawback to this setup is its poor accuracy in measurements of fluorescence intensity and, generally, its lack of spectral resolution in excitation and emission channels because of limitations of standard fluorescence microscopes. While it is possible to couple a fluorescence microscope with more sophisticated multi-wavelength excitation and emission channels, this is not a routine type of a fluorescence microscope and is extremely expensive to build.

One commercially available solution to enable observation of molecular layers absorbed on the inner glass surface of a sample cell using a standard horizontal-beam spectrofluorometer involves the use of triangular cells originally designed for measurements of samples with high optical density and/or turbidity. (See FIG. 2). Such cells are offered by the optical cell manufactures such as Starna Cells Inc. (See FIG. 3).

However, all of the cells that are currently manufactured have the front surface oriented at a 45 degree angle to the excitation channel, which creates a strong reflection of the excitation beam directly into the sensitive emission channel, effectively destroying signal-to-noise ratio of the measurement. Therefore, these triangular cells are not utilized for observation of molecular layers and are employed only in the analysis of turbid solutions when the fluorescence signal has a relatively high intensity.

Although unconventional cells having a non-45 degree angle relative to the excitation channel are not commercially available, such unconventional cells could be designed. However, an additional problem in using such unconventional cells would arise from the fact that the non-45-degree angle relative to the excitation beam would make the cells asymmetric such that the cell may be used only with the excitation beam coming from one specific side of the cell. This is problematic because many commercial spectrofluorometers have two excitation channels that illuminate the cell from opposite sides, for example, spectrofluorometers having a left channel equipped with a steady-state light source, and having a right channel equipped with a pulsed light source for time-domain measurements. Therefore, it would be impossible to perform steady-state and time-domain measurements on the same molecular sample using an unconventional cell having a non-45 degree angle. In this situation, the user would need to have two cells each made for the specific direction of the excitation light and create two identical samples in the two cells, which would complicate research design and increase costs.

Another important requirement for optical cells in biochemical research arises from the fact that sample quantities may be scarce for typical measurements. Therefore, there is a demand for so-called "microcells" such that the volume of the sample is within a microliter range (e.g., <100 μl). In order to utilize microcells in spectrofluorometers having 1-cm cell holders, adapters have been designed which center the microcell in the cell holder and provide reduced-size apertures for illumination and observation of the center of the sample solution while avoiding the cell corners (i.e., similar to illumination and emission screens).

Therefore, new microcell adapters for cell holders of spectrofluorometers are desirable. The new adapters preferably should receive and hold a microcell at a variable position (e.g., a variable skewed position) for detecting fluorescence of a sample at the inner surface of the microcell and permit use of the same microcell in spectrofluorometers that utilize multiple excitation channels for illuminating the microcell from opposite sides (e.g., from a right channel and from a left channel). The new adapters preferably should be configured for use in a commercially available spectrofluorometer having a 1-cm cell holder without having to modify the spectrofluorometer.

SUMMARY

Disclosed herein are spectrofluorometric adaptors for cell holders in spectrofluorometers and spectrofluorometric methods that enable fluorescence detection from surfaces of a microcell in conventional horizontal-beam spectrofluorometers equipped with standard cell holders and having multiple excitation channels.

The presently disclosed adapters are configured for a cell holder of a spectrofluorometer in which the cell holder is substantially square or rectangular in horizontal cross-section and the adapter includes an adapter body that fits into the cell holder. The cell holder and adapter body have centered, vertical axes which are substantially aligned.

The adapter body includes a cavity for receiving a microcell, which is a rectangular prism that is substantially square or rectangular in horizontal cross-section. The microcell has a centered, vertical axis such that when the microcell is positioned in the cavity of the adapter body, the vertical axis of the microcell may be offset relative to the vertical axes of the cell holder and adapter body and/or the microcell may be rotated horizontally about its vertical axis relative to the cell holder and adapter body. As such, the microcell may be turned about its vertical axis and/or horizontally shifted relative to the vertical axes of the cell holder and adapter body such that the excitation beam contacts the front wall and/or rear wall of the microcell and is observed by the emission channel from an orthogonal direction. In some embodiments, the excitation beam may contact the front wall and/or rear wall at an angle other than 90 degrees and at a position other than the center of the front wall and/or other than the center of the back wall of the microcell. In further embodiments, the microcell is placed in a horizontally skewed position relative to the cell holder, and generally, off-center to achieve illumination and observation of the cell wall instead the center of the cell volume. In even further embodiments, the axis of the microcell is aligned horizontally relative to the emission beam but shifted horizontally backward such that an inner wall of an emission side of the microcell is aligned in parallel with the excitation beam.

In some embodiments, the adapter body includes a substantially square or rectangular bottom having a bottom cavity for receiving the microcell and a substantially square or rectangular top having a top cavity for receiving the microcell. The bottom and top of the adapter body typically are connected by at least one vertical side between the bottom and the top that holds the bottom and top in square alignment. Preferably, the bottom and top of the adapter body are connected by at least two vertical sides, which optionally are two adjacent vertical sides that form a 90 degree angle, where the two vertical sides are between the bottom and the top of the adapter body and hold the bottom and top of the adapter body in square or rectangular alignment. The vertical sides of the adapter body typically include side windows that permit entrance of excitation light or exit of emission light. Optionally, the vertical sides include vertical slits for receiving an excitation window screen or an emission window screen that include a variable rectangular or linear slit therethrough permitting entrance of an excitation beam or exit of an emission signal.

In some embodiments, the bottom of the adapter body includes horizontal slits for receiving an insert where the insert, after being inserted, closes the bottom cavity for receiving the microcell, where the microcell sits on the insert and the insert prevents the microcell from passing through the bottom of the adapter body. Preferably, the adapter is vertically invertible in the cell holder where the top of the adapter body includes a slit for receiving the insert, similar to the bottom of the adapter body, such that the insert in the slit of the bottom is removable and replaceable to the slit of the top to open the bottom cavity and close the top cavity. The adapter then may be vertically inverted in the cell holder such that the top of the adapter is inverted such that it becomes the bottom of the adapter and the bottom of the adapter is inverted such that it becomes the top of the adapter. As such, in one vertical position, the adapter may be utilized to hold a microcell, illuminate the microcell from a left-hand excitation channel, and read the fluorescence at an emission channel. Subsequently, the microcell may be removed from the adapter, the adapter may be inverted to the opposite vertical position (i.e., by removing the insert at the bottom of the adapter body and replacing the insert to the top of the adapter body and inverting the adapter), the microcell may be replaced into the inverted adapter, the microcell may be illuminated from a right-hand excitation channel (e.g., at the identical incident angle and relative position to excitation beam as with the left-hand excitation channel), and the fluorescence may be read from an emission channel.

Also disclosed are methods for performing spectrofluorometric analysis. The methods optionally may utilize the presently disclosed adapters. In one method for performing a spectrofluorometric analysis on a sample as contemplated herein, the method includes: (a) placing the sample in a microcell, (b) placing the microcell in the adapter of as disclosed herein, (c) placing the adapter in the cell holder of the spectrofluorometer, and (d) performing the spectrofluorometric analysis. Suitable samples for this method may include fluorescent lipid bilayers that form on an interior surface of the microcell in which performing the spectrofluorometric analysis comprises detecting fluorescence at the interior surface of the microcell.

In another method for performing a spectrofluorometric analysis on a sample as contemplated herein, the method comprises: (a) placing the sample in a microcell, (b) placing the microcell in the invertible adapter as disclosed herein, (c) placing the adapter in the cell holder of the spectrofluorometer, (d) performing the spectrofluorometric analysis, (e) removing the microcell from the adapter, (f) inverting the adapter, (g) replacing the microcell into the adapter, and (h) performing the spectrofluorometric analysis. Suitable samples for this method may include fluorescent lipid bilayers that form on an interior surface of the microcell in which performing the spectrofluorometric analysis comprises detecting fluorescence at the interior surface of the microcell.

In another method for performing a spectrofluorometric analysis on a sample as contemplated herein, the method comprises: (a) placing a sample comprising lamellar vesicles in a microcell that is substantially square of rectangular in horizontal cross-section (i.e., not a microcell that is triangular in horizontal cross-section) and forming supported, fluorescent lipid bilayers on an interior surface of the microcell, (b) placing the microcell in an adapter, (c) placing the adapter in the cell holder of a spectrofluorometer, (d) performing the spectrofluorometric analysis by detecting fluorescence from the supported lipid bilayers at the interior surface of the microcell. In this method, the supported lipid bilayers may be formed by placing a solution or suspension comprising fluorescent lamellar vesicles in the microcell, allowing the fluorescent lamellar vesicles to contact the interior wall of the microcell and form supported, fluorescent lipid bilayers, flushing out the solution or suspension and excess fluorescent lamellar vesicles that have not attached to the interior wall of the microcell with a flushing solution that does not comprise the fluorescent lamellar vesicles, and refilling the microcell with the flushing solution. Flushing may be performed by introducing flushing solution in a manner that keeps the microcell filled with flushing solution during the entire flushing procedure.

BRIEF DESCRIPTION OF THE FIGURES

FIG. 1A. Illustration of fluorescence detection from a sample via excitation light and emission. FIG. 1B. Exemplary illumination schematic.

FIG. 4A, FIG. 4B, FIG. 4C, FIG. 4D, and FIG. 4E. Illustration of one embodiment of an adaptor as contemplated herein. Shown is an adapter with two horizontal sections at the top and the bottom with a square cavity to hold a microcell (see FIG. 4A). The microcell position with respect to the excitation window and emission window in this particular embodiment is shown in FIG. 4B. The adaptor may have an emission side with an aperture to expose a particular portion of the cell to the detector (see FIG. 4C). Variable apertures may be present in excitation screens and/or emission screens (FIG. 4C). inserted into vertical slits in the top section of the adapter and slid into the excitation window and/or emission window, respectively. The top section and the bottom section of the adaptor may include horizontal slits across the square cell cavity for positioning of a sliding insert (FIG. 4D) upon which the microcell may sit. FIG. 4E illustrates two views of a single working prototype of the 1-cm adaptor with the installed emission and excitation window screens, the sliding insert, and a standard Starna 3-mm microcell.

FIG. 7A. Rotatable holder including a microcell. FIG. 7B. Stationary plate. Directions of the excitation beam and emission window are indicated with the arrows on the plate. FIG. 7C. and FIG. 7D. Stationary and rotating plates assembled with different orientation of the cell with respect to the excitation and emission beams based on rotating the rotatable holder.

FIG. 8A, FIG. 8B, and FIG. 8C. Confocal microscopy imaging of supported lipid bilayers formed on the interior surface of the fluorometer cell. FIG. 8A. The rectangular quartz cell (3 mm path) on a sample platform to observe the inner cell wall facing the objective. FIG. 8B. Vertical cross-section of the microcell. The microscope was focused at three different vertical coordinates to image the slices above, at, and below the inner cell wall (positions I, II, and III, respectively). The cross section of the cell is schematically shown as a black line. The lipid bilayer location is indicated by the interior hatched line forming a square. The objective was centered at the vertical inner wall boundary to create strong contrast between the fluorescent cell content on the left and non-fluorescent optical material of the cell wall on the right of the image. The drawing is not to scale. FIG. 8C. Images of the 3 mm cell containing supported lipid bilayer including 1% (mol) of Rhodamine-DPPE taken with the 40× objective. The slices were imaged at three vertical positions (I, II, and III) of the confocal plane corresponding to the relative Z-coordinate of 25 µm, 0 µm, and −200 µm, respectively. Thickness of the optical section was 4.3 µm.

FIG. 9A, FIG. 9B, and FIG. 9C. Detection of fluorescence from supported lipid bilayers and evaluation of sensitivity of the method. FIG. 9A. Positioning of the rectangular 3 mm microcell inside the custom-designed cell adaptor. The excitation and emission channels are indicated by arrows, the light paths focused by optics and trimmed by custom slits are schematically depicted by dotted and solid lines. FIG. 9B. For comparison, schematic of the microcell placement in the standard 3 mm cell adaptor (Starna, Cat# FCA3) avoiding direct illumination of the front and rear inner cell walls. FIG. 9C. Solid line, the rhodamine emission spectrum of the supported lipid bilayer in the 3 mm microcell recorded using the custom adaptor shown in FIG. 9A. The bilayer was deposited utilizing 100 µM LUV containing 1% rhodamine-DPPE. Dashed line, the same sample was placed in the centered position of the FCA3 adaptor (per FIG. 9B) showing bilayer fluorescence excited by the light scattered in solution. Dash-dot-dash line, a reference 5 µM LUV solution with 1% rhodamine recorded in FCA3 adaptor (per FIG. 9B).

DETAILED DESCRIPTION

Figure 1A:
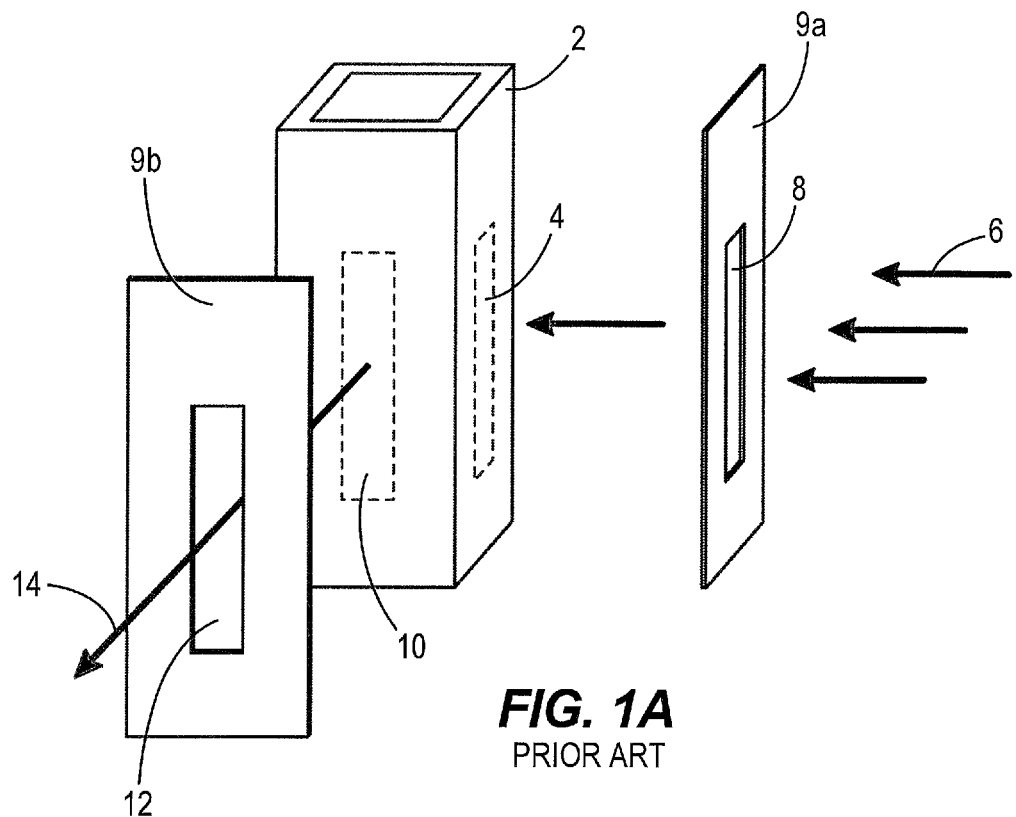
FIG. 1A and FIG. 1B. Convention horizontal-beam fluorescence configuration of the prior art.
Figure 1B:
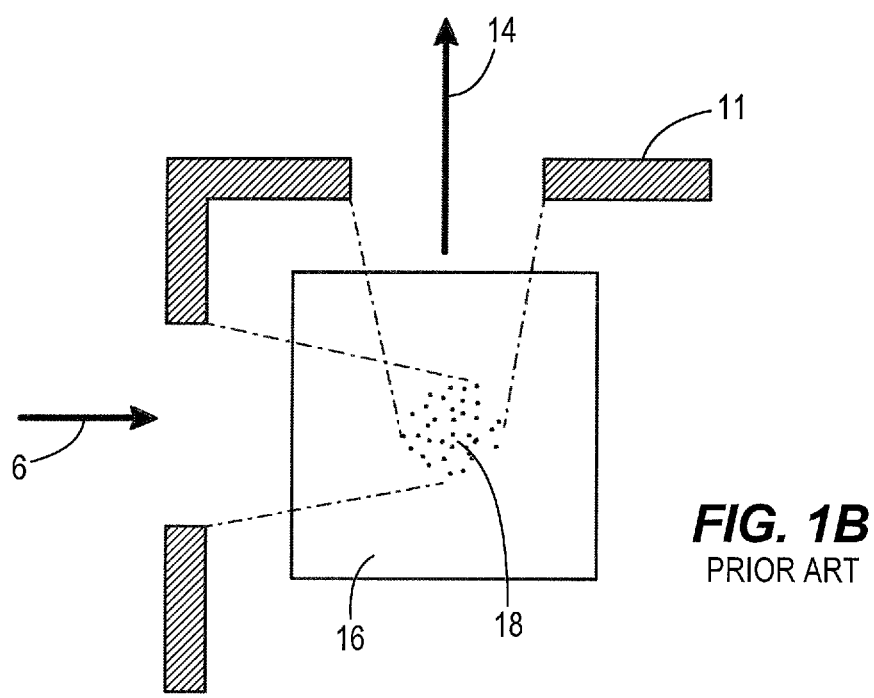
Figure 2:
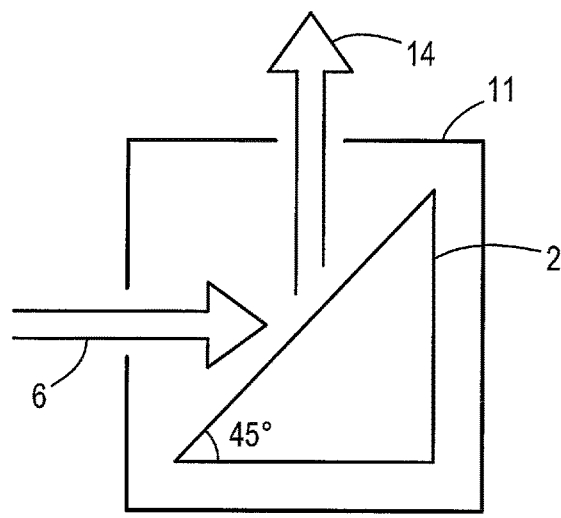
FIG. 2 Top view of a triangular cell having a 45 degree incident surface of the prior art.
Figure 3:
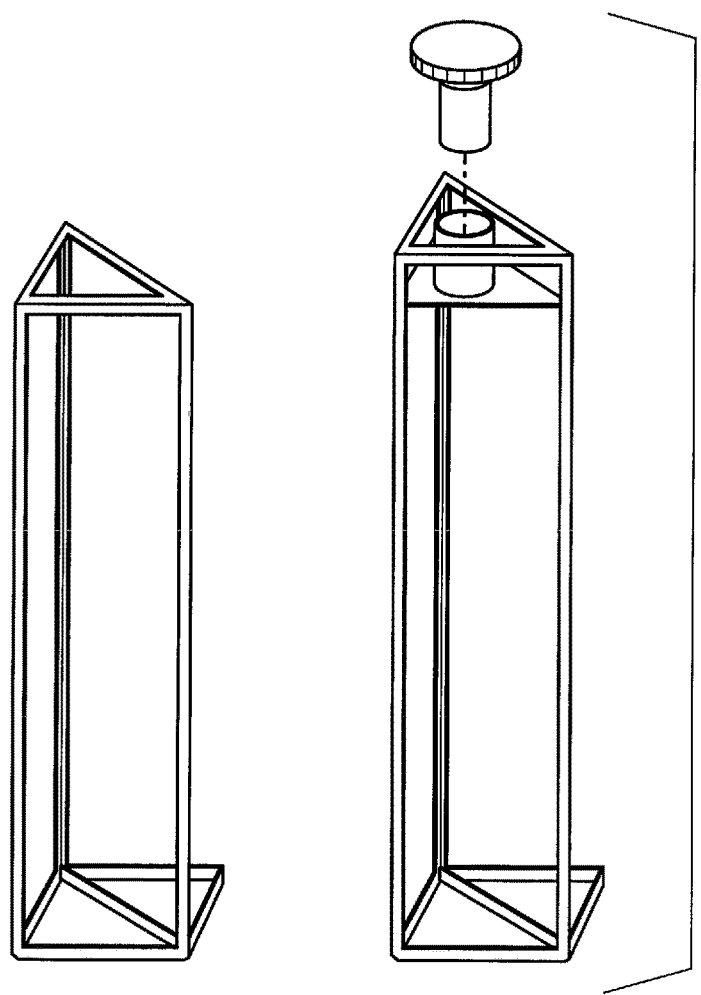
FIG. 3. Triangular cells manufactured by Starna Cells, Inc. and having a 45 degree incident surface of the prior art.

The disclosed subject matter further may be described utilizing terms as defined below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed subject matter relates to adapters for holding a cell in a spectrofluorometer. The presently disclosed adapters may be configured for use in a standard horizontal-beam spectrofluorometer with a typical cell holder (e.g., a 1-cm cell holder or another size) without having to modify the spectrofluorometer. The adapters are specifically configured for permitting observation of surface fluorescence in a microcell that is placed in the adapter. In some embodiments, the adapter comprises or consists of an adapter body with a cavity for receiving and holding a microcell, window screens with variable slits permitting entrance of excitation light and/or exit of emission light, and a removable bottom slit that is replaceable to the top of the adapter body such that the adapter is vertically invertible.

The adapter body positions a standard quartz or glass microcell at a selected angle relative to excitation and emission windows in the adapter body and relative to the cell holder.

The adapter body may include an excitation window screen and/or an emission window screen that include a variable rectangular or linear apertures therethrough permitting entrance of an excitation beam or exit of an emission signal. The variable rectangular or linear aperture limits entrance of the excitation beam to the selected surfaces of the microcell and limits exposure of selected portions of the illuminated surfaces of the microcell to the emission window, while minimizing scattering and reflection of the excitation light into the emission window. The angle and position of the microcell inside the body of the adaptor as well as the widths and positions of the rectangular or linear apertures may be adjusted to maximize intensity of the fluorescence signal and to reduce excitation light captured by the emission window.

To enable illumination and observation of fluorescence at the surface of the microcell, the microcell, generally, is positioned askew or off-center in the cell holder and at a variable angle (e.g., at an angle other than 0, 45, or 90 degrees) relative to the incident excitation beam, relative to the exit emission beam, and relative to the cell holder. In some embodiments, the microcell can be considered to be turned about a vertical axis relative to the incident excitation beam, relative to the exit emission beam, and relative to the cell holder. This configuration is inherently asymmetric and requires the excitation light to always enter from one specified direction. In other words, this configuration is impermissive of multiple excitation channels coming from different directions. Because standard fluorometers may have two independent excitation channels illuminating the microcell from opposite sides (i.e., left-hand excitation and right-hand excitation), the presently disclosed adaptor is designed to be "vertically invertible" (i.e., from top-to-bottom) with the microcell being inserted in one vertical end of the adapter for use with a first excitation channel and the microcell being inserted in the opposite vertical end of the adapter for use with the second excitation channel. To allow for the invertible design, an insert placed in horizontal slits at the bottom of the adaptor body is removable and may be re-positioned in horizontal slits at the top of the adapter body (i.e., the insert may be positioned at either vertical end of the adapter body to create a "top" or a "bottom" at either end for holding the microcell).

Referring now to the figures, FIG. 4A, FIG. 4B, FIG. 4C, and FIG. 4D illustrate one embodiment of an adaptor 15 as contemplated herein. Shown is an adapter 15 with two horizontal sections at the top 30a and the bottom 30b with a square cavity 22 to hold a microcell 2 (see FIG. 4A and FIG. 4B) and spaced vertically apart by an excitation side 50a and an emission side 50b at a 90 degree angle to the excitation side 50a. The adaptor 15 has an excitation side 50a with an excitation window 38 for receiving an excitation beam 6 which will contact a portion of a cell 2 within the adapter 15. The emission side 50b has an emission window 42 through which an emission beam 14 can be emitted and detected.

Figure 4D:
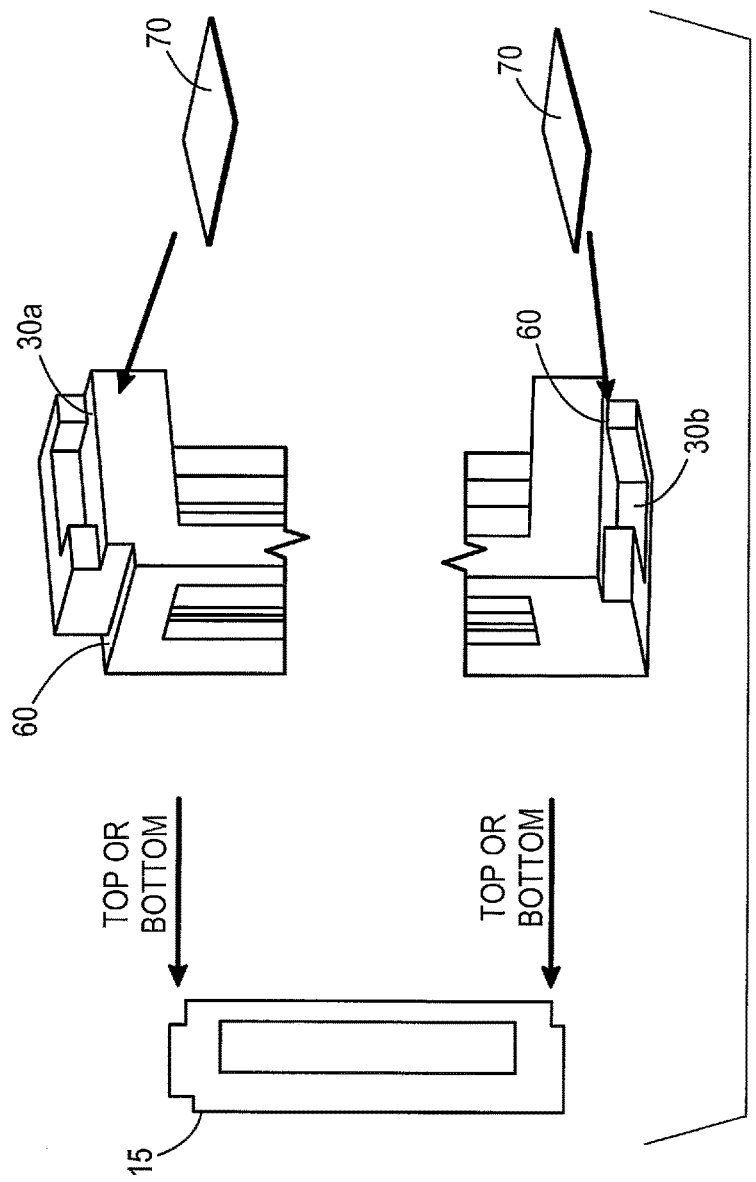
Figure 4C:
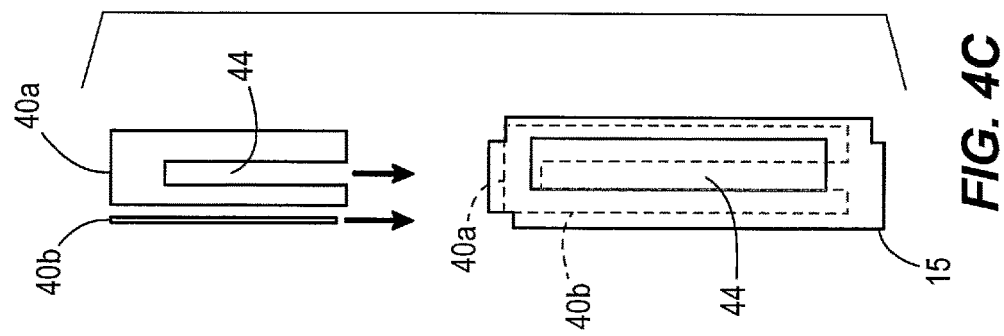

The amount of the microcell 2 exposed to the excitation beam 6 may be varied or adjusted by inserting an excitation screen 40a into a vertical slit 26 in the top section 30a of the adapter 15 (see FIG. 4C and FIG. 4D). As illustrated in FIG. 4C, the excitation screen 40a is slid into the vertical slit 26 of the adapter (see FIG. 4A) and covers a portion of the excitation window 38. The portion of the cell exposed to the excitation beam 6 can be varied by varying the size of the aperture 44 in the excitation screen 40a. The adapter 15 also may include a vertical slit (not shown) in the top section 30a for receiving an emission screen 40b. The emission screen 40b may be slid into the emission window 42 such that only a portion of the emission beam 14 is allowed to pass through the emission window 42 to the detector.

As illustrated in FIG. 4B, the microcell 2 is held by the adapter in a position that is askew, off-center, and/or turned about a vertical axis relative to a central vertical point or axis of the adapter 15 (i.e., which is defined by the intersection of an incident excitation beam 6 and an exit emission beam 14). As such, the adapter 15, when placed into a square cell holder will position the microcell 2 in the cell holder at a position that is askew, off-center, and/or turned about a vertical axis and/or at a variable angle (e.g., at an angle other than 0, 45, or 90 degrees) relative to the incident excitation beam 6, relative to the exit emission beam 14, and relative to the cell holder.

Figure 4E:
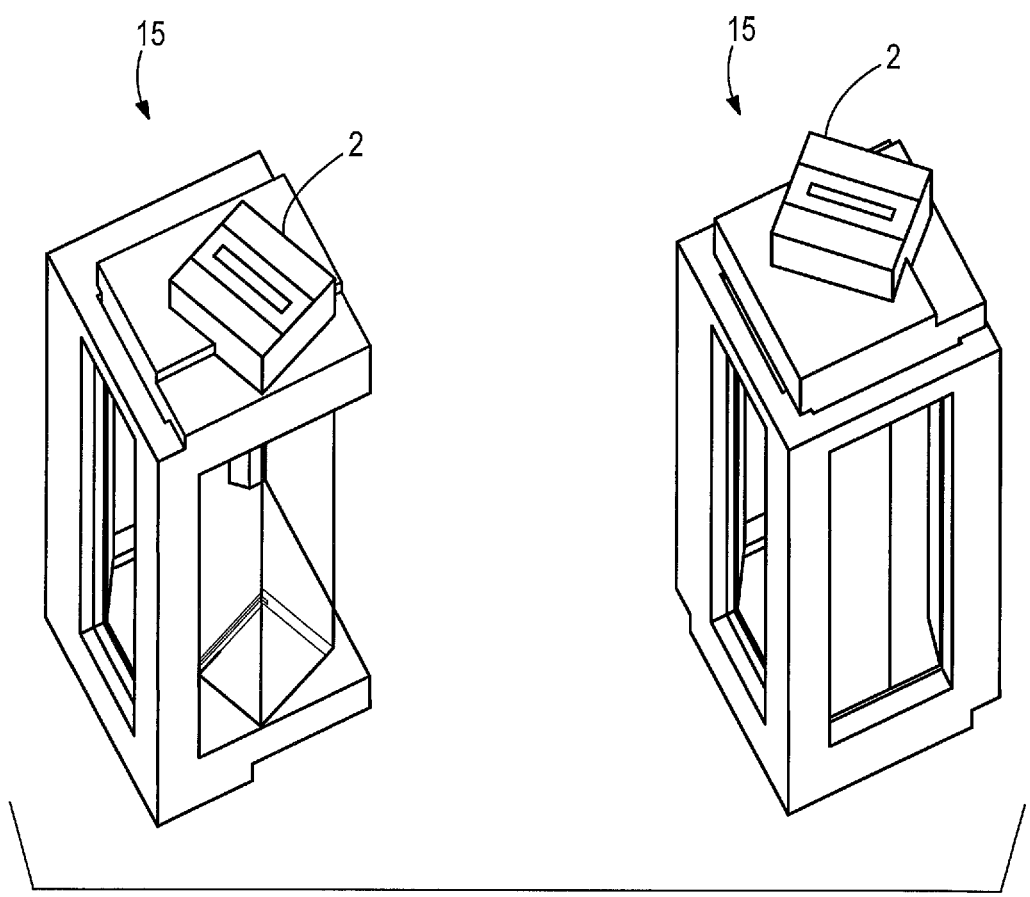

As illustrated in FIG. 4D, the adapter 15 may be vertically reversible. As illustrated, the top section 30a and the bottom section 30b of the adaptor 15 may include horizontal slits 60 across the square cavity 22 for inserting a sliding insert 70 in to the bottom section upon which the microcell 2 may sit. Subsequently, the microcell 2 may be removed from the bottom section 30b, the adapter 15 may be inverted vertically such that the top section 30a is now at the bottom of the adapter 15 and the sliding insert 70 may be replaced to the horizontal slit 60 of the top section 30a of the adapter 15, and the microcell 2 may be replaced into the square cavity 22 of the adapter 15 where the microcell 2 sits on the sliding insert 70. FIG. 4E illustrates two different prototypes having a microcell 2 inserted into an adapter 15.

Figure 5:
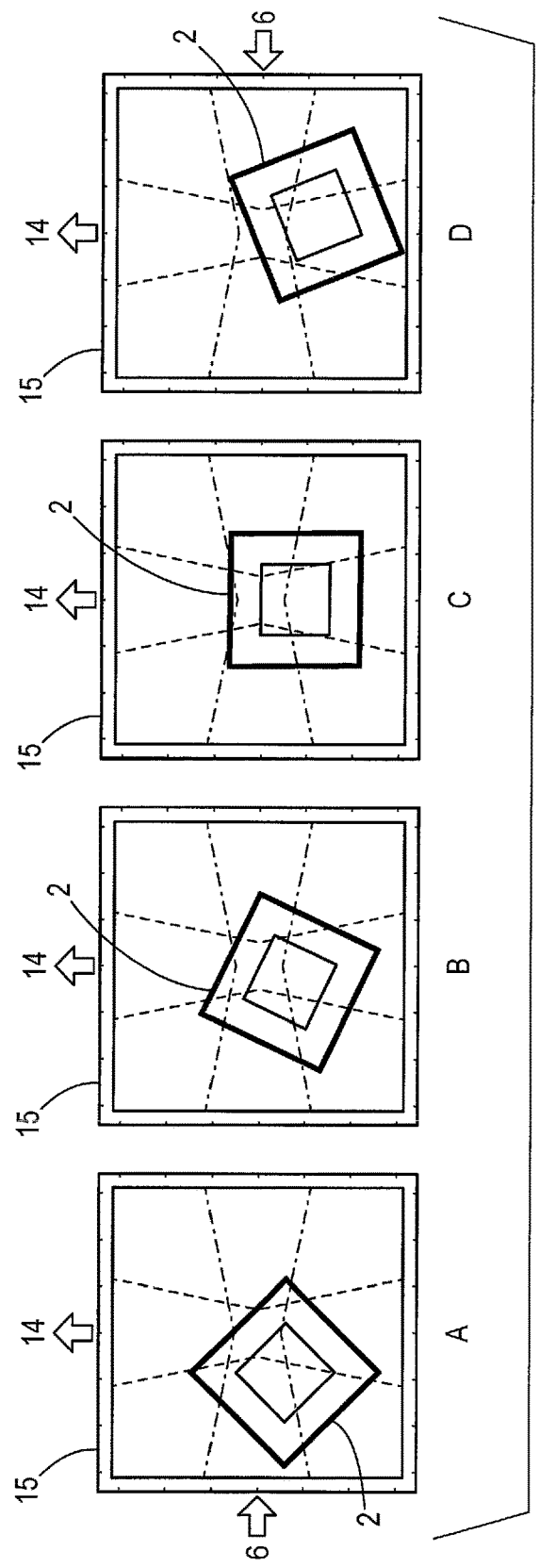
FIG. 5. Exemplary configurations regarding microcell placement and angle relative to excitation and emission channels.

The disclosed adapters may be configured to position a microcell at any selected position within a cell holder. FIG. 5 illustrates exemplary configurations of adapter and positioning of the microcell relative to the excitation beam 6 and emission beam 14. In panel A, the microcell 2 is turned and has its vertical central axis off-center relative to the vertical central axis of the adapter 15 (and relative to the vertical central axis of the cell holder). In panel B, the microcell 2 is turned and has its vertical central axis off-center relative to the vertical central axis of the adapter 15 (and relative to the vertical central axis of the cell holder). In panel C, the microcell 2 is horizontally aligned with the emission channel 14 (i.e., the emission channel 14 bisects the microcell 2), but the microcell 2 is shifted vertically downward with respect to excitation beam 6, effectively aligning the inside cell wall of the emission side of the microcell 2 in parallel with the excitation beam. In panel D, the adapter 15 has been vertically inverted and the microcell 2 is turned and has its vertical central axis off-center relative to the vertical central axis of the adapter 15 (and relative to the to the vertical central axis of the cell holder).

Figure 6A:
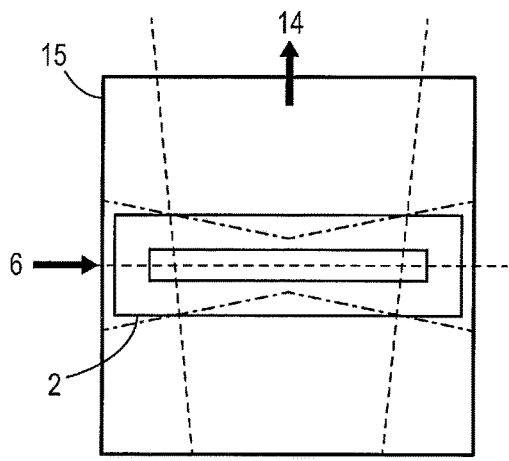
FIG. 6A, FIG. 6B, FIG. 6C, and FIG. 6D. Embodiments of orientations of a narrow-rectangle cell in an adaptor.
Figure 6B:
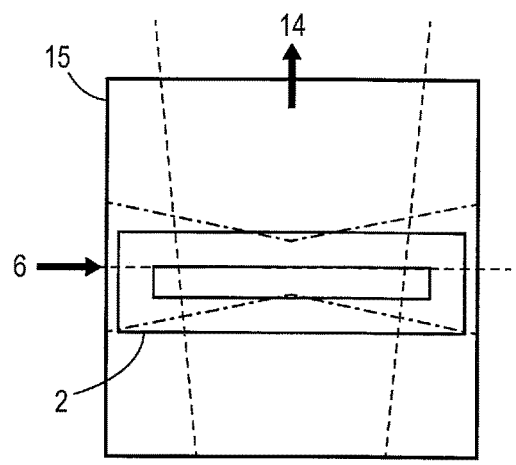
Figure 6C:
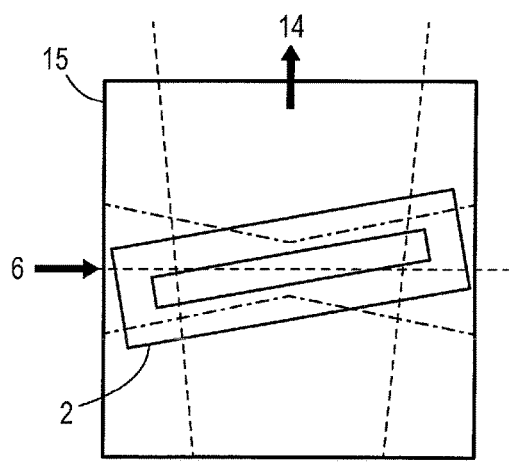
Figure 6D:
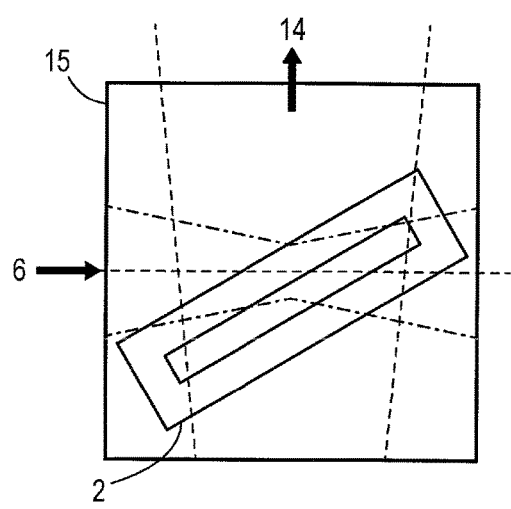

The disclosed adapters may be configured to receive and position a rectangular microcell at any selected position within a cell holder. FIG. 6A, FIG. 6B, FIG. 6C, and FIG. 6D illustrate embodiments of configurations of adapters for rectangular microcells and positioning of the microcells relative to the excitation beam 6 and emission beam 14. In FIG. 6A, the microcell 2 is aligned with the excitation beam 6 (i.e., where the excitation beam 6 bisects the microcell), and the microcell is aligned with the emission channel 14 (i.e., where the emission channel 14 bisects the microcell). In FIG. 6B, the microcell 2 is horizontally aligned with the emission channel 14 (i.e., where the emission channel 14 bisects the microcell), but the microcell 2 is shifted horizontally downward or backward with respect to the excitation beam 6, effectively aligning the inside cell wall of the emission side of the microcell 2 in parallel with the excitation beam 6. If FIG. 6C, the central vertical axis of the microcell 2 is aligned with the central vertical axis of the adapter 15 (and with the central vertical axis of the cell holder), but the microcell 2 is turned counter-clockwise about its central vertical axis relative to the adapter 15. In FIG. 6D, the vertical central axis of the microcell 2 is shifted downward or backward relative to the vertical central axis of the adapter 15, and the microcell 2 is turned counter-clockwise about its central vertical axis relative to the adapter 15.

Figure 7A:
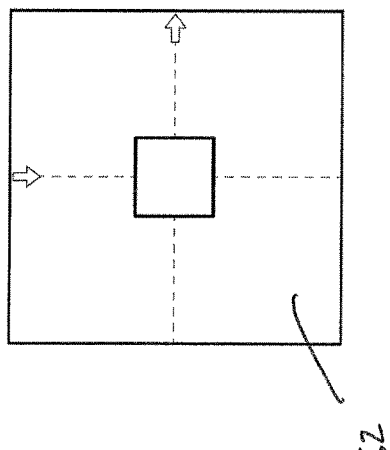
FIG. 7A, FIG. 7B, FIG. 7C, and FIG. 7D. Embodiment of the adapter to allow for adjustment of cell position and orientation directly in the fluorometer.
Figure 7B:
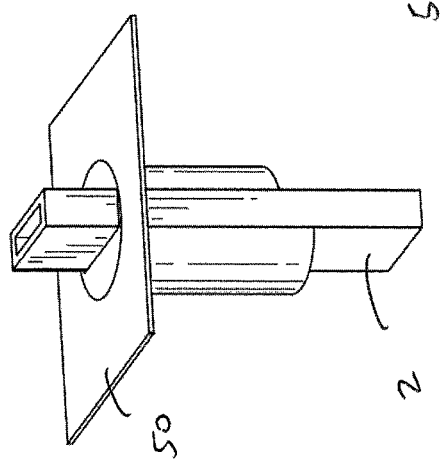
Figure 7D:
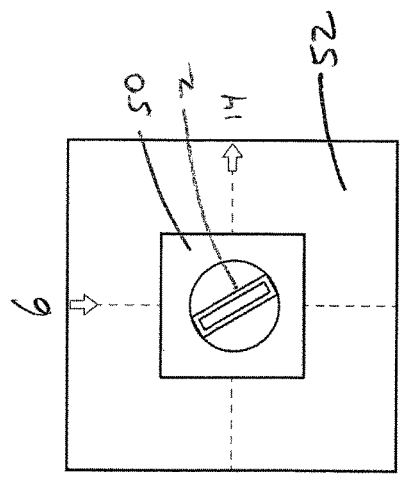
Figure 7C:
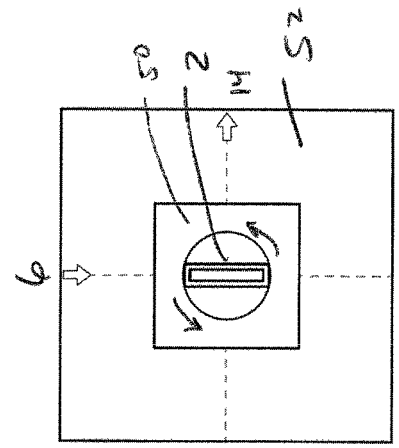

The adapter may be configured to rotate the microcell adjustably while the adapter holding the microcell is position in the cell holder. As illustrated in FIG. 7A, FIG. 7B, FIG. 7C, and FIG. 7D, the adapter includes a rotatable holder 50 (FIG. 7A) having an opening for inserting a microcell 2, and a stationary plate 52 (FIG. 7B). The rotatable holder 50 may be placed into the stationary plate 52 (FIG. 7C) and the stationary plate 52 may be inserted into a cell holder of a spectrofluorometer. The rotatable holder 50 may be rotated adjustably in order to rotate the inserted microcell 2 and vary the rotatable orientation of the microcell with respect to the excitation beam 6 and emission beam 14 (FIG. 7D), while the adapter is positioned in the cell holder.

As shown in FIG. 8A, the rectangular quartz cell (3 mm path) is positioned on a sample platform in order to observe the inner cell wall facing the objective. FIG. 8B, illustrates a vertical cross-section of the microcell. The microscope was focused at three different vertical coordinates to image the slices above, at, and below the inner cell wall (positions I, II, and III, respectively). The cross section of the cell is schematically shown as a black line, and the lipid bilayer location is indicated by the interior hatched line forming a square. The objective was centered at the vertical inner wall boundary to create strong contrast between the fluorescent cell content on the left and non-fluorescent optical material of the cell wall on the right of the image. The drawing is not to scale. As shown in FIG. 8C, images of the 3 mm cell containing supported lipid bilayer including 1% (mol) of Rhodamine-DPPE were taken with a 40× objective. The slices were imaged at three vertical positions (I, II, and III) of the confocal plane corresponding to the relative Z-coordinate of 25 µm, 0 µm, and −200 µm, respectively. Thickness of the optical section was 4.3 µm. The single dark line in FIG. 8C(I) indicates the position of the confocal plane at which the lipid bilayer is located. The diffuse image of FIG. 8C(II) represents imaging of the lipid bilayer where the vertical image position is aligned with the lipid bilayer. The image of FIG. 8C(III) is "blank" in that the lipid bilayer is not imaged.

Illustrative Embodiments

The following embodiments are illustrative and should not be interpreted to limit the scope of the claimed subject matter.

Embodiment 1

An adapter for a cell holder of a spectrofluorometer, the cell holder being substantially square or rectangular in horizontal cross-section, the adapter comprising a body that fits into the cell holder, the cell holder and adapter body having centered, vertical axes that are substantially aligned, the adapter body comprising a cavity for receiving a microcell, the microcell being a rectangular prism and being substantially square or rectangular in horizontal cross-section, the microcell having a centered, vertical axis such that the microcell may be positioned in the cavity of the adapter body such that at least one of the following conditions are met: (1) the vertical axis of the microcell is offset relative to the vertical axes of the cell holder and adapter body; (2) the microcell is rotated horizontally about its vertical axis relative to the cell holder and adapter body; and (3) the axis of the microcell is aligned horizontally relative to the emission beam but shifted horizontally backward such that an inner wall of an emission side of the microcell is aligned in parallel with the excitation beam.

Embodiment 2

The adapter of embodiment 1, wherein the microcell is positioned in the cavity of the adapter body such that both of condition (1) and condition (2) are met.

Embodiment 3

The adapter of embodiment 1 or 2, wherein the microcell is rotated horizontally about its vertical axis relative to the cell holder and adapter body at an angle relative to the cell holder that is not 45 degrees.

Embodiment 4

The adapter of any of the foregoing embodiments, wherein the adapter body comprises a substantially square or rectangular bottom having a bottom cavity for receiving the microcell, a substantially square or rectangular top having a top cavity for receiving the microcell, and at least one vertical side between the bottom and the top and holding the bottom and top in square or rectangular alignment.

Embodiment 5

The adapter of embodiment 4, comprising at least two vertical sides between the substantially square or rectangular bottom and the substantially square or rectangular top and holding the bottom and top in square or rectangular alignment.

Embodiment 6

The adapter of embodiment 5, wherein the two vertical sides are adjacent and form a 90 degree angle.

Embodiment 7

The adapter of any of embodiments 4-6, wherein the vertical side comprises a side window permitting entrance of excitation light or exit of emission light.

Embodiment 8

The adapter of embodiment 7, wherein the vertical sides comprise vertical slits for receiving an excitation window screen or an emission window screen, the window screens including apertures for permitting entrance or exit of light.

Embodiment 9

The adapter of any of embodiments 4-8, wherein the bottom comprises horizontal slits for receiving an insert, the insert closing the bottom cavity for receiving the microcell and preventing the microcell from passing through the bottom of the adapter.

Embodiment 10

The adapter of embodiment 9, wherein the adapter is vertically invertible in the cell holder, wherein the top comprises a slit for receiving the insert such that the insert in the slit of the bottom is removable and replaceable to the slit of the top to open the bottom cavity and close the top cavity, and the adapter then is vertically inverted in the cell holder such that the top is inverted to the bottom and the bottom is inverted to the top.

Embodiment 11

The adapter of any of the foregoing embodiments, wherein the adapter comprises a rotatable holder into which the microcell is inserted.

Embodiment 12

The adapter of embodiment 11, wherein the adapter further comprises a stationary plate into which the rotatable holder is inserted, and optionally the stationary plate is attached to the body of the adapter or is an integral part of the adapter body.

Embodiment 13

A method for performing a spectrofluorometric analysis on a sample, the method comprising: (a) placing the sample in a microcell, (b) placing the microcell in the adapter of any of the foregoing embodiments, (c) placing the adapter in the cell holder of the spectrofluorometer, and (d) performing the spectrofluorometric analysis.

Embodiment 14

The method of embodiment 13, wherein the sample comprises a fluorophore-labelled lipid bilayer that forms on an interior surface of the microcell and performing the spectrofluorometric analysis comprises detecting fluorescence at the interior surface of the microcell.

Embodiment 15

A method for performing a spectrofluorometric analysis on a sample, the method comprising: (a) placing the sample in a microcell, (b) placing the microcell in the invertible adapter of embodiment 10, (c) placing the adapter in the cell holder of the spectrofluorometer, (d) performing the spectrofluorometric analysis, (e) removing the microcell from the adapter, (f) inverting the adapter, (g) replacing the microcell into the adapter, and (h) performing the spectrofluorometric analysis.

Embodiment 16

The method of embodiment 15, wherein the sample comprises a fluorophore-labelled lipid bilayer that forms on an interior surface of the microcell and performing the spectrofluorometric analysis comprises detecting fluorescence at the interior surface of the microcell.

Embodiment 17

A method for performing a spectrofluorometric analysis on a sample comprising supported lipid bilayers, the method comprising: (a) placing a sample comprising fluorophore-labelled lamellar vesicles in a microcell that is substantially square or rectangular in cross-section and forming supported, fluorophore-labelled lipid bilayers on an interior surface of the microcell, and (b) detecting fluorescence from the supported fluorophore-labelled lipid bilayers at the interior surface of the microcell.

Embodiment 18

The method of embodiment 17, wherein the supported lipid bilayers are formed by placing a solution or suspension comprising fluorescent lamellar vesicles in the microcell, allowing the fluorescent lamellar vesicles to attach to the interior wall of the microcell and form supported, fluorescent lipid bilayers, flushing out the solution or suspension and excess fluorescent lamellar vesicles that have not attached to the interior wall of the microcell with a flushing solution that does not comprise the fluorescent lamellar vesicles in a manner that keeps the microcell filled with flushing solution during the entire flushing procedure.

Embodiment 19

The method of embodiment 17 or 18, wherein detecting fluorescence comprises contacting the interior surface of the microcell with an excitation beam of the spectrofluorometer and exposing the interior surface of the microcell to the emission channel of the spectrofluorometer.

Embodiment 20

The method of embodiment 19, wherein the microcell is placed in an adapter and inserted into a spectrofluorometer prior to detecting fluorescence from the supported lipid bilayers at the interior surface of the microcell, and the adapter comprises internal slits that trim the excitation beam of the spectrofluorometer and expose the interior surface of the microcell to the emission channel.

EXAMPLES

The following examples are illustrative and should not be interpreted to limit the scope of the claimed subject matter.

Example 1

The presently disclosed adapter may be utilized in methods for detecting fluorescence from molecular layers absorbed on the inner surfaces of a fluorometer microcell using a standard horizontal beam fluorometer equipped with a standard 1-cm cell holder. The detection of fluorescence on the inner surfaces of the microcell is enabled by (1) placing the microcell at a specific position and angle with respect to the excitation and emission windows with the aid of the disclosed adaptor inserted in the cell holder, and (2) utilizing customized screens having variable apertures at specific positions in windows of the adapter body that control excitation and emission paths through the adaptor and microcell to optimize the ratio of fluorescence-to-scatter light intensity. The adapter may be used to position the fluorometer microcell inside the fluorometer cell holder off-center and/or at an angle in order to appropriately expose the surfaces of the microcell to the excitation and emission channels. The desired positioning of the microcell is achieved by the adapter body and square or rectangular cavity therein which may be askew or angled (i.e., turned about a vertical axis) relative to the incident excitation beam, relative to the exit emission beam, and relative to the cell holder. As such, when the microcell is placed in the cavity, the microcell and the surfaces of the microcell are positioned askew or angled (i.e., turned about a vertical axis) relative to the incident excitation beam, relative to the exit emission beam, and relative to the cell holder. FIG. 4A illustrates one embodiment of the adaptor showing two horizontal sections at the top and the bottom with a square cavity to hold the microcell. The microcell position with respect to the excitation and emission windows in this particular embodiment is shown in FIG. 4B.

In FIG. 4B, the excitation light illuminates the inner surface of the microcell and causes fluorescence that is observed through the emission window. The width of the aperture in the window screen and the position of the window screen in the excitation path are adjustable to restrict illumination to specific cell surface(s). Black hatched bars in FIG. 4B indicate window screen portions blocking the light, and the opening between them is an aperture that allows the excitation light to illuminate the specified portion of the cell. Likewise, the side of the adaptor facing the emission channel (i.e. light detector) has a variable aperture to expose a particular portion of the cell to the detector. The variable apertures may be present in window screens (FIG. 4C) inserted into the vertical slits in the emission and excitation sides of the adaptor as in FIG. A or the variable apertures may be an integral part of the vertical sides of the adaptor body provided the variable aperture allow for illumination and/or observation of specific cell areas.

Particular combinations of aperture widths, aperture positions, positioning of the microcell inside the holder, and the angle of the microcell relative to the excitation beam may be selected to increase intensity of the observed fluorescence signal from inner surfaces while reducing contributions from the scattered and reflected light of the excitation beam.

The top and the bottom of the adaptor feature narrow horizontal slits across the cell cavity for positioning of the sliding insert (FIG. 4D) upon which the microcell may sit. As such, the sliding insert prevents the microcell from passing through the bottom of the adapter. The insert may be placed at either end of the adaptor (i.e., the top end or the bottom end) to enable use of the adapter in spectrofluorometers having multiple excitation channels (e.g., in spectrofluorometers having right-sided and left-sided excitation channels). Therefore, only one adaptor is required for use in a two-channel spectrofluorometer. FIG. 4E illustrates two working prototypes of the 1-cm adaptor with the installed emission and excitation window screens, the sliding insert, and a standard Starna 3-mm microcell.

The configuration of the adapter and the window screens may vary depending on the geometry of the excitation beam. For example, when the excitation beam is a well-focused steady-state source, the adapter may utilize a window screen having a relatively narrow aperture on the excitation side to avoid strong reflections from the edges of the microcell. On the other hand, when the excitation beam is a pulsed LED, the adapter may utilize a window screen having a relatively wide aperture or the adapter may not utilize a window screen at all to facilitate illumination of the cell surfaces. Some exemplary configurations are illustrated in FIG. 5.

In some embodiments, the disclosed adapters may be utilized in experiments that include analyzing fluorescence from bilayer molecular structures that are immobilized on the inner surface of a microcell. The bilayer molecular structures are immobilized on the inner surface thus enabling analysis of interactions of different ligands with the bilayer and its protein components in variable conditions. Multiple experiments are possible by repeatedly exposing the same bilayer to a series of biochemical agents. The proposed adaptor is a low-cost solution to advance academic research on membrane proteins in supported lipid bilayers, and to facilitate development of clinical tests for membrane protein function.

REFERENCES

1. Galush et al. (2008), "Quantitative fluorescence microscopy using support lipid bilayer standards," Biophy J. 95, 2512-9.
2. Crane et al. (2007), "Fluorescence Microscopy to Study Domains in Supported Lipid Bilayers." In Method in Membrane Lipids, Vol. 400, pp. 481-488.
3. Lakowicz, J. R. (2010) Principles of Fluorescence Spectroscopy. $3^{rd}$ edit. Springer.
4. U.S. Pat. No. 8,115,922.

Example 2

Another embodiment of the disclosed adaptor is designed to utilize a microcell that has a rectangular cross-section with one narrow and another long dimension. FIG. 6A, FIG. 6B, FIG. 6C, and FIG. 6D demonstrate the horizontal cross-section of this embodiment of the adapter with a narrow-rectangle cell positioned in different orientations in the adapter with respect to the excitation beam. In FIG. 6A, FIG. 6B, FIG. 6C, and FIG. 6D, the horizontal cross-section of the square cell adaptor is shown with a black outline. The outer and inner boundaries of the microcell also are shown. The excitation light beam focused by optics of the excitation channel and trimmed by adaptor slits is schematically shown with horizontally slanted dash-dot-dash lines. Horizontal dashed line indicates center of the excitation light beam (which is schematically shown with horizontally slanted dash-dot-dash lines) and serves as a reference for the cell position. The portion of the cell exposed to the emission channel is indicated with vertically slanted dashed lines.

As illustrated in FIG. 6A, Position A allows the inner cell walls to be illuminated at a very sharp angle due to the fact that optics is adjusted to focus the beam in the middle of the cell holder. The sharp angle of the incident excitation light leads to a very small amount of scattering into the emission channel thus increasing sensitivity. In addition, due to elongated geometry of the cell, the cell corners are located outside of the area observed by the emission channel. In this position both inner cell walls are illuminated to a similar degree because the cell is centered with respect to the cell holder. As illustrated in FIG. 6B, Position B improves illumination of one inner cell wall (i.e., the front cell wall as illustrated) by shifting the cell backward in the adapter to increase efficiency of excitation of fluorophores absorbed at the front, inner cell wall. As illustrated in FIG. 6C, Position C further increases intensity of light hitting the inner cell wall by rotating the cell counter-clockwise in the adapter where the cell is rotated about a center point (defined by the intersection of the center axis of the excitation channel and the center axis of the emission channel). As illustrated in FIG. 6D, Position D reduces scattering from the left cell corner by rotating the cell in the adapter about a skewed point (i.e., where the cell is moved from the center point of the adaptor and rotated counter-clockwise).

The disclosed narrow-rectangle microcell of this embodiment may provide advantages over a square microcell. First, the useful surface that may be exposed to the emission channel in a narrow-rectangle microcell is wider. For example, the cross-section cell of the narrow-rectangle microcell is 10 mm wide while the cross-section of the square microcell is only 3 mm. Also, the corners of the narrow-rectangle microcell are located farther away from the center of the emission window, and thus are less likely to contribute to scattering. Slanted dashed lines in FIG. 6A, FIG. 6B, FIG. 6C, and FIG. 6D indicate an approximately useful width for an emission window using the narrow-rectangle microcell. Further, the inner front and back walls of the narrow-rectangle microcell are separated by a relatively small distance (e.g., 1 mm) such that both inner cell walls (i.e., front inner cell wall and back inner cell wall) will be exposed to the excitation beam in most orientations of the microcell in the adapter.

This effectively doubles the amount of useful fluorescence signal emitted from the sample layers absorbed on these inner walls, therefore increasing sensitivity of detection when the narrow-rectangle microcell is used.

Example 3

In some embodiments of the disclosed adapters, the position and orientation of the cell in the adapter may be adjustable, for example, to correct for small variation in tuning of the focusing optics of some fluorometers. Accurate illumination of the inner cell surfaces is sensitive to such variability and may be addressed by either providing a set of adaptors with different cell position, which the end user will be able to choose from to obtain maximum signal, or by using a direct position-adjustment mechanism. One prototype of such a mechanism of the adapter to allow for adjustment of cell position and orientation directly in the fluorometer is shown in FIG. 7A, FIG. 7B, FIG. 7C, and FIG. 7D. The prototype of FIG. 7A, FIG. 7B, FIG. 7C, and FIG. 7D includes a rotatable holder including a microcell (see FIG. 7A). The prototype of FIG. 7A, FIG. 7B, FIG. 7C, and FIG. 7D also includes a stationary plate, where directions of the excitation beam and emission window are indicated by the arrows on the plate (see FIG. 7B). The rotatable holder may be inserted into the stationery plate (FIG. 7C) and the microcell may be rotated at different orientations (FIG. 7D) with respect to the excitation and emission beams.

The stationary plate may be mounted on top of a fluorometer cell holder and may have a square opening aligned with the cavity of the cell holder. The stationary plate may include downward flaps extending into the cell holder downwardly from the plate surface to keep the stationary plate fixed at all times in the cell holder. The rotatable holder including a microcell may be inserted into the opening of the stationary plate until the cell reaches the bottom of the cell holder and the rotatable holder rests on top of the stationary plate. In this example, the microcell is positioned vertically in the cell holder (see FIG. 7C). The horizontal position of the microcell and its angle relative to the excitation and emission beams are easily adjusted by rotating the rotatable holder, and hence the microcell, relatively to the stationary plate. The optimal position (e.g., as evaluated by the maximum useful fluorescence signal and minimum scattering) may be marked on the stationary plate, which allows this position to be reproduced for future readings with necessary precision. Using the recorded angle and position parameters, the adaptor body may be manufactured with the matching location of the cell cavity resulting in non-adjustable optimized adaptor. Alternatively, the cell-position adjustment may be performed for every particular experiment using the described mechanism for adjusting the position of the microcell or a similar mechanism.

Example 4

Reference is made to the attached manuscript entitled "Fluorescence of supported phospholipid bilayers recorded in a conventional horizontal-beam spectrofluorometer," E. A. Kovrigina, and E. L. Kovrigin, *Journal of Fluorescence*, 2016 March; 26(2):379-83, the content of which is incorporated herein by reference in its entirety.

Title: Fluorescence of Supported Phospholipid Bilayers Recorded in a Conventional Horizontal-Beam Spectrofluorometer Abstract Supported phospholipid bilayers are a convenient model of cellular membranes in studies of membrane biophysics and protein-lipid interactions. Traditionally, supported lipid bilayers are formed on a flat surface of a glass slide to be observed through fluorescence microscopes. This paper describes a method to enable fluorescence detection from the supported lipid bilayers using standard horizontal-beam spectrofluorometers instead of the microscopes. In the proposed approach, we form the supported lipid bilayers on the inner optical surfaces of the standard fluorescence microcell. To enable observation of the bilayer absorbed on the cell wall, the microcell is placed in a standard fluorometer cell holder and specifically oriented to expose the inner cell walls to both excitation and emission channels with a help of the custom cell adaptor. In our measurements, the signal intensity from supported bilayers doped with 1% (mol) of rhodamine-labeled lipid in the standard 3-mm optical microcell was equivalent to fluorescence of the 70-80 nM reference solution of rhodamine recorded in a commercial microcell adaptor. Because no modifications to the instruments are required in this method, a variety of steady-state and time-domain fluorescence measurements may be performed with supported phospholipid bilayers using standard horizontal-beam spectrofluorometers.

Introduction

Supported phospholipid bilayers were long established as a model of cellular phospholipid membranes [1]. The phospholipid bilayers attached to the glass surface (with and without cross-linking to the glass) are physically very similar to other membrane mimics in their biophysical properties [2]. The main approach to recording fluorescence signals from such supported bilayers is through the microscopes with the bilayer deposited on the horizontal surface of the glass slide and covered by a layer of the aqueous buffer [3,4]. Fluorescence microscopy of supported bilayers allows analysis of spontaneous phase separation [5,6] as well as detection of molecular events at the bilayer with a single-molecule resolution [7,8]. One highly useful feature of the supported lipid bilayer (relatively to liposomes) is that it is immobilized allowing for dynamic replacement of the solution in contact with the bilayer. Supported lipid bilayers are routinely studied in the flow-cell mode with the microscopy setups to reveal interactions of membrane proteins with lipids and with soluble ligands (for example, [9,10]). However, if one is particularly interested in spectral properties of the lipid-associated fluorophores and their changes due to ligand interactions, the microscopes must use multi-wavelength lasers and include detectors with spectral resolution, which are expensive and not generally available (for the example of such setup see [11]). The best practical approach to record fluorescence of lipid bilayers in standard spectrofluorometers was to utilize solutions (suspensions) of liposomes or protein-liposome complexes [12-15]. Yet, liposomes are not very stable and do not allow for easy replacement of the surrounding buffer as they are freely diffusing particles. Supported lipid bilayers represent a convenient alternative because they are easily prepared by spontaneous fusion of lipid vesicles with the glass surfaces [1,2] yet require use of sophisticated fluorescence microscopes for their analysis. This paper reports a proof-of-principle experiment where a supported lipid bilayer is created in a standard fluorometer microcell and fluorescence measurements are performed in a typical horizontal-beam spectrofluorometer. We believe that this inexpensive approach may serve a number of needs in studies membrane protein interactions with lipids and soluble ligands.

Material and Methods

Preparation of Liposomes

Lipid mixtures contained DOPC:DOPG:fluorophore in the molar ratio of 89:10:1. Rhod-DPPE was used as a fluorescent marker of the lipid bilayer. All lipids were obtained from Avanti Polar Lipids Inc. and used without further purification. Large unilamellar vesicles (LUV) were prepared by extrusion through 0.2 µm polycarbonate membrane using Avanti Mini-Extruder. The total concentration of lipids during extrusion was 1 mM. The lipids were diluted to 0.1 mM for deposition of the supported lipid bilayers. Use of LUV versus multi-lamellar vesicles (MLV) or small unilamellar vesicles (SUV) does not appear to be a strict requirement in this protocol; Brian and McConnell [1] successfully utilized MLV in their pioneer work while SUV were employed by Cremer and Boxer [16] for the same purpose.

Preparation of Supported Lipid Bilayers

Supported lipid bilayers were formed on the inner surface of a rectangular 3-mm fluorometer microcell (Starna #3-3.45-Q-3) by completely filling the cell with the LUV solution of 0.1 mM total lipid (a minimum concentration allowing for the stable bilayer formation [1,5,16]). Bilayers with negatively charged lipids were reported to form very fast at physiological pH and ionic strength [16]. To keep the bilayer adhered to the walls, the cell must stay filled at all times because air-water boundary destroys the attached bilayers [16]). Therefore, to remove the initial LUV solution, we flushed the cell with a continuous flow of the phosphate saline buffer. To perform the flush, the cell was positioned horizontally and the buffer was introduced towards the bottom of the cell with the needle; the displaced solution was allowed to exit the cell and drip into the waste container. Capillary forces were sufficient to keep cells completely filled during the entire procedure. Relatively wide spacing between walls in the microcell (3 mm) made the buffer exchange process somewhat inefficient—50 to 100 ml of buffer at a flow rate (approx.) 2 ml/min was required to ensure complete removal of residual LUV from the bulk solution inside the microcell. Quality of the LUV removal was checked by residual fluorescence of the bulk solution in the microcell.

Confocal Fluorescence Microscopy

Images of supported lipid bilayers were taken using Nikon Perfect Focus Ti-E inverted research microscope. To support the 3 mm cell in horizontal position in front of the objective, the custom cell holder was utilized.

Fluorescence Spectroscopy

Photon Technologies International QuantaMaster 40 spectrofluorometer (Horiba) was used for recording emission spectra from supported lipid bilayers. The fluorometer was equipped with a standard 1 cm sample holder, emission and excitation monochromators, and Xenon steady-state excitation source. A custom cell adaptor was designed to hold the standard 3 mm microcell from Starna (Cat#3-3.45-Q-3). The adaptor included internal slits to trim the excitation beam and to expose the illuminated cell surface to the emission channel. Details of the adaptor design are described in the U.S. Provisional Patent Applications No. 62/079,273 and No. 62/186,449 filed with U.S. Patent Office on Nov. 13, 2014 and Jun. 30, 2015, respectively.

Results

Visualization of the Supported Lipid Bilayers

Prior to spectroscopic investigation, formation of supported lipid bilayers on the inner surfaces of the fluorometer cell may be confirmed using fluorescence microscopy. FIG. 8A, FIG. 8B, and FIG. 8C show representative rhodamine fluorescence images of the inner volume of the 3-mm rectangular microcell. The sample platform was adjusted such that left-hand-side of the image corresponds to interior of the optical cell, while the right-hand-side is always inside the material of the vertical cell wall (FIG. 8A and FIG. 8B). To demonstrate that the fluorescent lipids are found exclusively on the inner walls for the optical cell and not in the solution, we imaged confocal planes at three vertical coordinates (FIG. 8B and FIG. 8C). The position III is 200 μm below the inner wall and shows no fluorescence as the confocal plane is entirely localized inside the horizontal cell wall. The position II is aligned with the inner surface of the horizontal cell wall and reveals bright fluorescence (left of the cell wall junction) corresponding to rhodamine in the phospholipid bilayer coating the inner cell surface. The uppermost position I is 25 μm above the inner surface of horizontal cell wall intersecting the vertical inner cell surface in the middle of the image. Left-hand-side of the image revealed no significant fluorescence from solution inside the cell indicating that all suspended LUV were successfully removed by flushing procedure. The bright straight line in the middle originates from fluorescence of the supported lipid bilayer formed on the vertical inner cell wall. Real thickness of the lipid bilayer cannot be estimated from these images due to inherent resolution limit of optical spectroscopy of about 400 nm at this wavelength. Therefore, we relied on literature reports that the absorbed lipids form a bilayer with the expected thickness of about 5 nm as was previously established [5,16]. Black area on the right of the image corresponds to the non-fluorescent interior of the vertical cell wall (see FIG. 8C, Position (I)).

Supported Lipid Bilayers in a Horizontal-Beam Spectrofluorometer

Figure 9C:
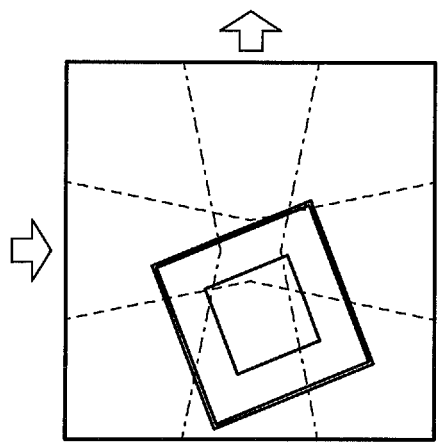
Figure 9C:
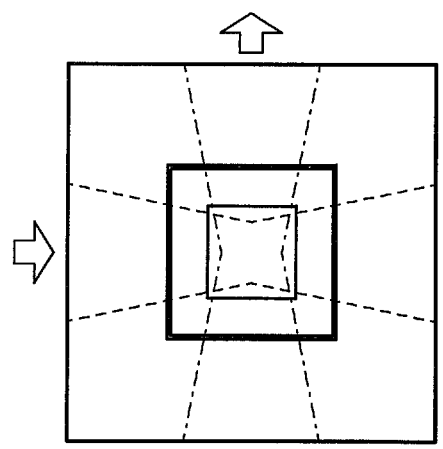
Figure 9C:
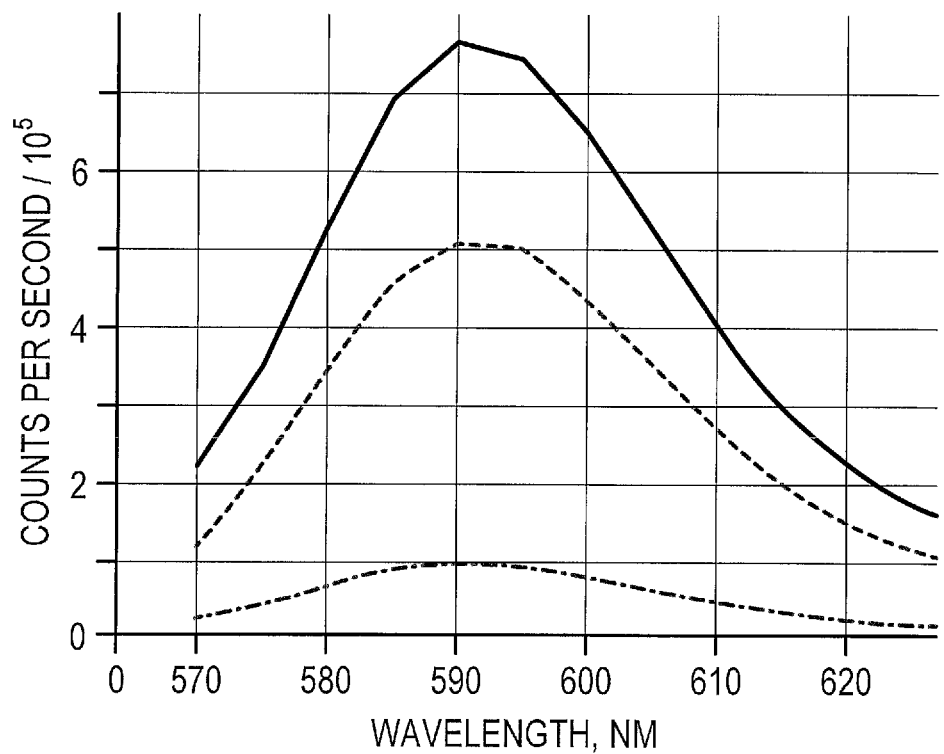

For observation of fluorescence from phospholipid bilayers we set the microcell inside the standard 1-cm cell holder to expose the surface with the bilayer to both excitation and emission channels. FIG. 9A shows one of the possible positions of the microcell for bilayer observation compared to the standard centered position (FIG. 9B). FIG. 9C gives emission spectra recorded from the supported lipid bilayers and the diluted reference LUV solution. In this measurement, we used 560 nm excitation light with identical 5-nm slits in the excitation and emission monochromators. Illumination of the surface of the cell (Panel A) generates both the useful fluorescence from the surface and scattered light from the corners of the microcell; therefore, one has to use additional adjustable slits trimming the excitation beam as well as limiting exposure of the emission channel to cell edges. Solid line in Panel C shows fluorescence signal from the most optimal combination of cell position and adjustable slits. This optimal combination is likely to slightly vary from one instrument to another due to differences in tuning of the focusing optics.

To confirm that the recorded fluorescence comes from the supported bilayer rather than from any residual LUV in the bulk solution, we tested the solution fluorescence from the same sample using a standard microcell adaptor with a centered cell location (FCA3, Starna) shown in Panel C. The FCA3 adaptor is manufactured to enable observation of fluorescence from internal volume of the solution, and its narrow windows shield corners of the cell from exposure to excitation and emission channels. In our supported bilayer preparation we flushed the microcell with a buffer in several stages, every time recording residual LUV fluorescence from the bulk solution in the microcell using FCA3 adaptor. After passing about 50 ml of buffer through the cell, we observed the rhodamine fluorescence drop to a minimum value shown as a dash-dot-dash line in FIG. 9C. Further flushing with another 50 ml did not reduce it any more indicating that this residual fluorescence signal likely comes from the supported bilayers on the front and back walls (facing the emission channel) excited indirectly by the light scattered in solution.

Relative sensitivity of measurements from the supported lipid bilayer sample may be evaluated by comparison of its fluorescence to the signal intensity of a reference LUV solution in a centered adaptor FCA3. The dash-dot-dash black line in FIG. 9C is a spectrum of the initial LUV solution used for preparation of supported lipid bilayers diluted to 5 μM total lipid concentration prior to the measurement (resulting in 50 nM concentration of rhodamine). Thus, the signal from supported lipid bilayers with 1% (mol) rhodamine in a 3-mm microcell was equivalent to 70-80 nM of rhodamine in LUV solution (recorded with 5 nm excitation and emission slits in the 3-mm cell).

DISCUSSION

Typical applications of supported lipid bilayers utilized glass slides or flow-cells positioned horizontally to observe the bilayers from below or above in some kind of a microscopy setup. Supported lipid bilayers formed on the inner surfaces of the fluorometer cells may be investigated while oriented vertically because van der Waals forces holding the bilayers in place are stronger than gravity while the optical cell ensures that the bilayer is covered with solution at all times. In our experiments, supported lipid bilayer samples were stable for more than a week at 4° C. Vertical orientation of lipid bilayers in our method has another advantage over the horizontal orientation: biomolecular aggregates (or dust) sediment to the bottom of the microcell, thus leaving the observation area. With the supported lipid bilayers located horizontally in the microscopy setups, all aggregates settle directly onto the bilayer under study thus potentially biasing measurement results.

Observation of fluorescence from the solution near the cell surface dates back as far as to Sir Frederick William Herschel who described fluorescence of optically dense quinine solutions [17]. Since then the solutions of high optical density or/and significant turbidity were routinely studied with illumination of the cell surface at an angle such that the incident light penetrates a thin layer of solution inside the cell, which fluoresces. These applications typically utilize triangular cells with the cell surface oriented at the 45° angle to both emission and excitation channels. This arrangement, however, is not suitable for fluorescence detection from supported lipid bilayers because the weak fluorescence signal is swamped with the excitation light reflected into the monochromator thus destroying the signal/noise ratio. Lakowicz recommended smaller 20-30° angles to reduce scattered light with such triangular cells [18]—this is approximately the angle we are using in FIG. 9A. However, the optical cells that would expose the front cell surfaces to the excitation beam at these sharp angles are not generally available. Utilizing the commercial microcell that is smaller than the size of the standard 1-cm cell holder allowed us to explore multiple positions and orientations of the cell achieving illumination of the cell surfaces at different angles.

Another requirement in biochemical applications is a small size of the sample. The triangular 45° cells manufactured by Starna or Hellma require 1.7 ml of solutions to fill. Here we utilized a 3-mm Starna microcell, which nominally holds 315 µL of a sample bringing it to the volume range of flow-cells in microscopy applications. By attaching a cell cap with the needle and inlet-outlet tubing one might construct a flow cell to be able to replace solution in the cell directly in the fluorometer (in this study, for the sake of simplicity, we were flushing the cell outside of the instrument).

It has been demonstrated that proteoliposomes may be used to create supported lipid bilayers incorporating membrane proteins [1,2]. In our method, by adding the ligand to the bulk solution one may perform titration studies of receptor-ligand interactions. Subsequent flushing out the ligand regenerates the unbound form of the membrane-associated receptor thus allowing for multiple repeated experiments with the same bilayer sample.

Standard spectrofluorometers are often equipped with temperature-controlled cell holders opening an avenue for studies of temperature-dependent thermodynamic and kinetic properties of the supported bilayer samples. One may note that a potential alternative way of exposing supported bilayers at the cell surfaces to the excitation and the emission channels at different angles could be to utilize the solid sample holder with a microcell adaptor. However, the solid sample holders cannot be thermostatted due to their open design thus precluding studies of membrane proteins, which require accurate temperature control. The described method with placement of the optical microcell inside the standard enclosed 1-cm cell holder allows for effective heat transfer between the cell holder and the sample enabling experiments at different temperatures.

The proposed approach to observation of the supported bilayer fluorescence is also agnostic to the type of the excitation light source, therefore time-domain studies are equally possible on the same samples used for spectral recording. In summary, a combination of a straightforward bilayer-forming technique, commercial optical cells coupled with the simple custom adaptors, and the standard spectrofluorometer hardware allows for an inexpensive way of recording fluorescence from supported lipid bilayers thus facilitating detailed studies of lipid membranes, membrane proteins, and their interactions with the time-domain and spectral resolution.

REFERENCES

1. Brian A A, McConnell H M (1984) Allogeneic stimulation of cytotoxic T cells by supported planar membranes. Proc Natl Acad Sci USA 81: 6159-6163.
2. Tamm L K, McConnell H M (1985) Supported phospholipid bilayers. Biophysical Journal 47: 105-113.
3. Bagatolli L A (2007) Membranes and Fluorescence Microscopy. In: C. D. Geddes (ed.), editor. Reviews in Fluorescence. pp. 33-51.
4. Galush W J, Nye J A, Groves J T (2008) Quantitative fluorescence microscopy using supported lipid bilayer standards. Biophys J 95: 2512-2519.
5. Crane J M, Tamm L K (2007) Fluorescence Microscopy to Study Domains in Supported Lipid Bilayers. Methods in Membrane Lipids. pp. 481-488.
6. Pinto S N, Fernandes F, Fedorov A, Futerman A H, Silva L C, et al. (2013) A combined fluorescence spectroscopy, confocal and 2-photon microscopy approach to re-evaluate the properties of sphingolipid domains. Biochimica Et Biophysica Acta-Biomembranes 1828: 2099-2110.
7. Hell S W, Wichmann J (1994) Breaking the diffraction resolution limit by stimulated emission: stimulated-emission-depletion fluorescence microscopy. Optics Letters 19: 780-782.
8. Kastantin M, Walder R, Schwartz D K (2012) Identifying Mechanisms of Interfacial Dynamics Using Single-Molecule Tracking. Langmuir 28: 12443-12456.
9. Lin W-C, Iversen L, Tu H-L, Rhodes C, Christensen S M, et al. (2014) H-Ras forms dimers on membrane surfaces via a protein—protein interface. Proceedings of the National Academy of Sciences 111: 2996-3001.
10. Iversen L, Tu H-L, Lin W-C, Christensen S M, Abel S M, et al. (2014) Ras activation by SOS: Allosteric regulation by altered fluctuation dynamics. Science 345: 50-54.
11. Raicu V, Singh D R (2013) FRET Spectrometry: A New Tool for the Determination of Protein Quaternary Structure in Living Cells. Biophysical Journal 105: 1937-1945.
12. Kinnunen P, Alakoskela J-M, Laggner P, Nejat D (2003) Phase Behavior of Liposomes. Methods in Enzymology: Academic Press. pp. 129-147.
13. Janoff A S (1999) Liposomes: Rational Design: Marcel Dekker.
14. Walden P (1994) Liposomes as tools for the reconstitution of biological systems. In: Philippot J. R. SF, editor. Liposomes as tools in basic research and industry. Boca Raton: CRC Press. pp. 71-88.
15. Woodle M C, Papahadjopoulos D (1989) Liposome preparation and size characterization. Methods Enzymol 171: 193-217.
16. Cremer P S, Boxer S G (1999) Formation and Spreading of Lipid Bilayers on Planar Glass Supports. The Journal of Physical Chemistry B 103: 2554-2559.
17. Herschel F W (1845) On a case of superficial colour presented by a homogeneous liquid internally colorless. Philosophical Transactions of the Royal Society of London 135: 143-145.
18. Lakowicz J R (2010) Principles of Fluorescence Spectroscopy: Springer. 954 p.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

I claim:

1. An adapter for a cell holder of a spectrofluorometer, the cell holder being substantially square or rectangular in horizontal cross-section, the adapter comprising a body that fits into the cell holder, the cell holder and adapter body having centered, vertical axes that are substantially aligned, the adapter body comprising a cavity for receiving a microcell, the microcell being a square or rectangular prism being substantially square or rectangular in horizontal cross-section, the microcell having a centered, vertical axis such that the microcell may be positioned in the cavity of the adapter body such that at least one of the following conditions are met: (1) the vertical axis of the microcell is offset relative to the vertical axes of the cell holder and adapter body; (2) the microcell is rotated horizontally about its vertical axis relative to the cell holder and adapter body; and (3) the axis of the microcell is aligned horizontally relative to the emission beam but shifted horizontally backward such that an inner wall of an emission side of the microcell is aligned in parallel with the excitation beam.

2. The adapter of claim 1, wherein the microcell is positioned in the cavity of the adapter body such that both of condition (1) and condition (2) are met.

3. The adapter of claim 1, wherein the microcell is rotated clockwise or counter-clockwise about its vertical axis relative to the cell holder and adapter body at an angle relative to the cell holder that is not 45 degrees.

4. The adapter of claim 1, wherein the adapter body comprises a substantially square bottom or rectangular bottom having a bottom cavity for receiving the microcell, a substantially square top or rectangular top having a top cavity for receiving the microcell, and at least one vertical side between the bottom and the top and holding the bottom and top in square or rectangular alignment.

5. The adapter of claim 4, comprising at least two vertical sides between the substantially square bottom or rectangular bottom and the substantially square top or rectangular top and holding the bottom and top in square or rectangular alignment.

6. The adapter of claim 5, wherein the two vertical sides are adjacent and form a 90 degree angle.

7. The adapter of claim 4, wherein the vertical side comprises a side window permitting entrance of excitation light or exit of emission light.

8. The adapter of claim 7, wherein the vertical sides comprise vertical slits for receiving an excitation window screen or an emission window screen, the window screens including apertures for permitting entrance or exit of light.

9. The adapter of claim 4, wherein the bottom comprises horizontal slits for receiving an insert, the insert closing the bottom cavity for receiving the microcell and preventing the microcell from passing through the bottom of the adapter.

10. The adapter of claim 9, wherein the adapter is vertically invertible in the cell holder, wherein the top comprises a slit for receiving the insert such that the insert in the slit of the bottom is removable and replaceable to the slit of the top to open the bottom cavity and to close the top cavity, and the adapter then is vertically inverted in the cell holder such that the top is inverted to the bottom and the bottom is inverted to the top.

11. The adapter of claim 1, wherein the adapter comprises a rotatable holder into which the microcell is inserted.

12. The adapter of claim 11, wherein the adapter further comprises a stationary plate into which the rotatable holder is inserted.

13. A method for performing a spectrofluorometric analysis on a sample, the method comprising: (a) placing the sample in a microcell, (b) placing the microcell in the adapter of claim 1, (c) placing the adapter in the cell holder of the spectrofluorometer, and (d) performing the spectrofluorometric analysis.

14. The method of claim 13, wherein the sample comprises a fluorophore-labelled lipid bilayer that forms on an interior surface of the microcell and performing the spectrofluorometric analysis comprises detecting fluorescence at the interior surface of the microcell.

15. A method for performing a spectrofluorometric analysis on a sample, the method comprising: (a) placing the sample in a microcell, (b) placing the microcell in the invertible adapter of claim 10, (c) placing the adapter in the cell holder of the spectrofluorometer, (d) performing the spectrofluorometric analysis, (e) removing the microcell from the adapter, (f) inverting the adapter, (g) replacing the microcell into the adapter, and (h) performing the spectrofluorometric analysis.

16. The method of claim 15, wherein the sample comprises a fluorophore-labelled lipid bilayer that forms on an interior surface of the microcell and performing the spectrofluorometric analysis comprises detecting fluorescence at the interior surface of the microcell.

17. A method for performing a spectrofluorometric analysis on a sample comprising supported lipid bilayers, the method comprising: (a) placing a sample comprising fluorophore-labelled lamellar vesicles in a microcell that is substantially square or rectangular in cross-section and forming supported, fluorophore-labelled lipid bilayers on an interior surface of the microcell, and (b) detecting fluorescence from the supported fluorophore-labelled lipid bilayers at the interior surface of the microcell.

18. The method of claim 17, wherein the supported lipid bilayers are formed by placing a solution or suspension comprising fluorescent lamellar vesicles in the microcell, allowing the fluorescent lamellar vesicles to attach to the interior wall of the microcell and form supported, fluorescent lipid bilayers, flushing out the solution or suspension and excess fluorescent lamellar vesicles that have not attached to the interior wall of the microcell with a flushing solution that does not comprise the fluorescent lamellar vesicles in a manner that keeps the microcell filled with flushing solution during the entire flushing procedure.

19. The method of claim 17, wherein detecting fluorescence comprises contacting the interior surface of the microcell with an excitation beam of the spectrofluorometer and exposing the interior surface of the microcell to the emission channel of the spectrofluorometer.

20. The method of claim 19, wherein the microcell is placed in an adapter and inserted into a spectrofluorometer prior to detecting fluorescence from the supported lipid bilayers at the interior surface of the microcell, and the adapter comprises internal slits that trim the excitation beam of the spectrofluorometer and expose the interior surface of the microcell to the emission channel.

* * * * *